US008716021B2

(12) United States Patent
Aladjem et al.

(10) Patent No.: US 8,716,021 B2
(45) Date of Patent: May 6, 2014

(54) USE OF REPLICATORS TO PREVENT GENE SILENCING

(75) Inventors: Mirit I. Aladjem, Potomac, MD (US); Cindy Tseng, Sandy Spring, MD (US); Haiqing Fu, Rockville, MD (US); Lixin Wang, Charlottesville, VA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1014 days.

(21) Appl. No.: 12/066,076

(22) PCT Filed: Sep. 7, 2006

(86) PCT No.: PCT/US2006/034812
§ 371 (c)(1),
(2), (4) Date: Mar. 6, 2008

(87) PCT Pub. No.: WO2007/030588
PCT Pub. Date: Mar. 15, 2007

(65) Prior Publication Data
US 2008/0274550 A1    Nov. 6, 2008

Related U.S. Application Data

(60) Provisional application No. 60/715,113, filed on Sep. 7, 2005.

(51) Int. Cl.
*C12N 15/63*    (2006.01)
*C12N 15/90*    (2006.01)
*C07H 21/04*    (2006.01)

(52) U.S. Cl.
USPC ........ 435/455; 435/462; 435/320.1; 536/24.1

(58) Field of Classification Search
USPC ...................... 435/455, 463, 320.1; 536/24.1
See application file for complete search history.

(56) References Cited

U.S. PATENT DOCUMENTS

| 6,524,851 | B1 | 2/2003 | Ellis |
| 6,906,041 | B2 | 6/2005 | Braun |
| 6,977,174 | B2 | 12/2005 | Crouzet et al. |
| 6,995,006 | B2 | 2/2006 | Atkinson et al. |
| 7,002,027 | B1 | 2/2006 | Engler et al. |
| 7,005,277 | B2 | 2/2006 | Imler et al. |

FOREIGN PATENT DOCUMENTS

| WO | WO 00/12693 | 3/2000 |
| WO | WO 01/94629 | 12/2001 |
| WO | WO 03/064641 | 8/2003 |

OTHER PUBLICATIONS

Lin et al Current Biology, 2003, (13), 1019-1028.*
Schildkraut et al Nature Biotechnology, 2006, 24(5), 523-524).*
Thomas et al. Nature Rev.Genet. 4: 346-358; 2003.*
Verma et al Annu Rev Biochem. 2005;74:711-38.*
Fu et al Nature Biotechnology 24, 572-576, 2006.*
Liu et al Molecular and Cellular Biology, 2003, 23(5), 1832-1842.*
Wang et al Molecular and Cellular Biology, 2004, 3373-3386.*
Wang et al., Mol Cell Biol 24:3373, 2004, 337-338.*
Altman and Fanning, Mol Cell Biol. 24 (10):4138-50, 2004.*
Philpott et al. (2004) Human Gene Ther., vol. 15, 47-61.*
Aladjem et al., Genetic dissection of a mammalian replicator in the human beta-globin locus. Science. Aug. 1998; 281(5379): 1005-1009.
Aladjem et al., The replicon revisited: an old model learns new tricks in metazoan chromosomes. EMBO Rep. Jul. 2004;5(7):686-91.
Fu et al., Preventing gene silencing with human replicators. Nature Biotechnology. May 2006; 24(5): 572-576.
Lin et al., Dynamic Alterations of Replication Timing in Mammalian Cells. Current Biology. Jun. 2003; 13(12): 1019-1028.
Liu et al., Multiple functional elements comprise a mammalian chromosomal replicator. Mol. and Cell. Bio. Mar. 2003; 23(5): 1832-1842.
Palacios DeBeer et al., A role for a replicator dominance mechanism in silencing. EMBO Journal. Jul. 18, 1999(13): 3808-3819.
Schildkraut et al., Replicators lessen transcriptional silencing. Nature Biotechnology. 2006, 24(5): 523-524.
Aladjem et al., "Replication Initation Patters in the β-Globin Loci of Totipotent and Differentiated Murine Cells: Evidence for Multiple Initation Regions," *Mol. Cell. Biol.*, 22(2):442-452, 2002.
Aladjem, "The Mammalian Beta Globin Origin of DNA Replication," *Front Biosci.*, 9:2540-2547, 2004.
Altman et al., "Defined Sequence Modules and an Architectural Element Cooperate to Promote Initiation at an Ectopic Mammalian Chromosomal Replication Origin," *Mol. Cell. Biol.*, 24(10):4138-4150, 2004.
Altman et al., "The Chinese Hamster Dihydrofolate Reductase Replication Origin Beta Is Active at Multiple Ectopic Chromosomal Locations and Requires Specific DNA Sequence Elements for Activity," *Mol. Cell. Biol.*, 21(4):1098-1110, 2001.
Bailis et al., "It's All in the Timing: Linking S Phase to Chromatin Structure and Chromosome Dynamics," *Cell Cycle*, 2(4):303-306, 2003.
Buzina et al., "Initation of DNA replication at the human β-globin 3' enhancer," *Nuc. Acids Res.*, 33:14, 4412-4424, 2005.
Caddle et al., "Analysis of the autonomous replication behavior in human cells of the dihydrofolate reductase putative chromosomal origin of replication," *Nucleic Acids Research*, 20(22):5971-5978, 1992.
Cimbora et al., "Long-Distance Control of Origin Choice and Replication Timing in the Human β-Globin Locus Are Independent of the Locus Control Region," *Mol. Cell. Biol.*, 20(15):5581-5591, 2000.
CRISP abstract for NHLBI grant No. 5K01HL003141-10 (2004); Maria Del Pilar Aguinaga.
Feng et al., "Position Effects Are Influenced by the Orientation of a Transgene with Respect to Flanking Chromatin," *Mol. Cell. Biol.*, 51(1):298-309, 2001.

(Continued)

*Primary Examiner* — Anne Marie S Wehbe
(74) *Attorney, Agent, or Firm* — Klarquist Sparkman, LLP

(57) ABSTRACT

Regulatory elements, specifically replicators and transgene constructs containing replicator nucleic acid sequences, are disclosed herein. Methods of using replicators and transgene constructs including replicators to inhibit, delay, or prevent gene silencing are also disclosed herein.

18 Claims, 9 Drawing Sheets

(56) References Cited

OTHER PUBLICATIONS

Feng et al., "The Human β-Globin Locus Control Region Can Silence as Well as Activate Gene Expression," *Mol. Cell. Biol.*, 52(10):3864-3874, 2005.

Fu et al., "Genetic and Epigenetic Control of DNA Replication at the Human Beta Globin Locus," Cold Spring Harbor Symposium, Sep. 7-11, 2005.

Gilbert, "Replication timing and transcriptional control: beyond cause and effect," *Curr. Opin. Cell Biol.*, 14(3):377-83, 2002.

Haase et al., "Replication control of autonomously replicating human sequences," *Nucleic Acids Research*, 19(18):5053-5058, 1991.

Hu et al., "Identification of novel initiation sites for human DNA replication around ARSH1, a previously characterized yeast replicator," *Biochem. Biophys. Res. Commun.*, 131(4):1058-64, 2004.

Krysan et al., "Autonomous Replication in Human Cells of Multimers of Specific Human and Bacterial DNA Sequences," *Mol. Cell. Biol.*, 13(5):2688-2696, 1993.

Lu et al., "Functionally distinct, sequence-specific replicator and origin elements are required for *Drosophila chorion* gene amplification," *Genes & Dev.*, 15:134-146, 2001.

Malott et al., "Activity of the c-myc Replicator at an Ectopic Chromosomal Location," *Mol. Cell. Biol.*, 19(8):5685-5695, 1999.

Paixão et al., "Modular Structure of the Human Lamin B2 Replicator," *Mol. Cell. Biol.*, 24(7):2958-2967, 2004.

Schaarschmidt et al., "An episomal mammalian replicon: sequence-independent binding of the origin recognition complex," *The EMBO Journal*, 23(1):191-201, 2004.

Tower, "Developmental Gene Aplification and Origin Regulation," *Annual Review of Genetics*, 38:273-304, 2004.

Wang et al., "The Human β-Globin Replication Initiation Region Consists of Two Modular Independent Replicators," *Mol. Cell. Biol.*, 24(8):3373-3386, 2004.

Weinreich et al., "The activities of eukaryotic replication origins in chromatin," *Biochimica et Biophysica Acta*, 1677:142-157, 2004.

Westphal et al., "A System for Shuttling 200-kb BAC/PAC Clones into Human Cells: Stable Extrachromosomal Persistence and Long-Term Ectopic Gene Activation," *Human Gene Therapy*, 9:1863-1873, 1998.

* cited by examiner

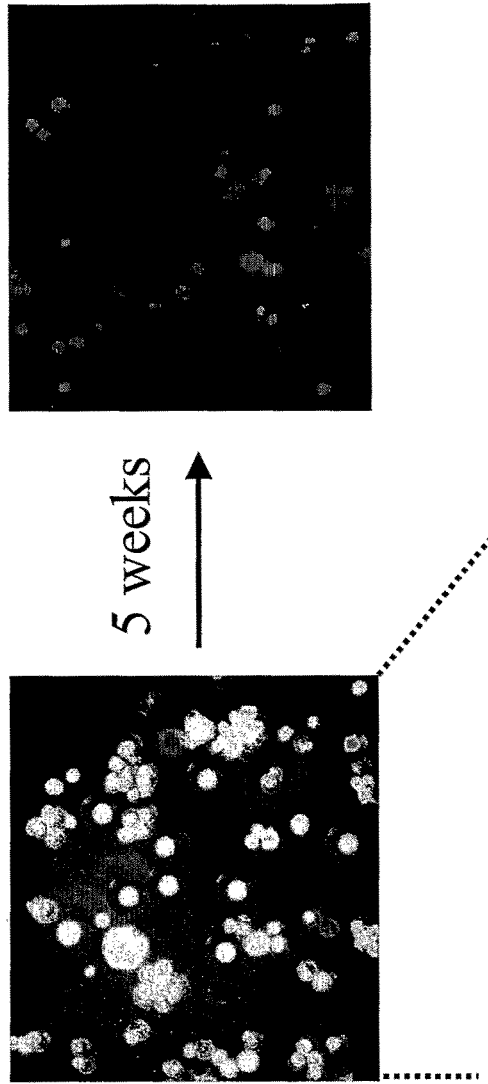
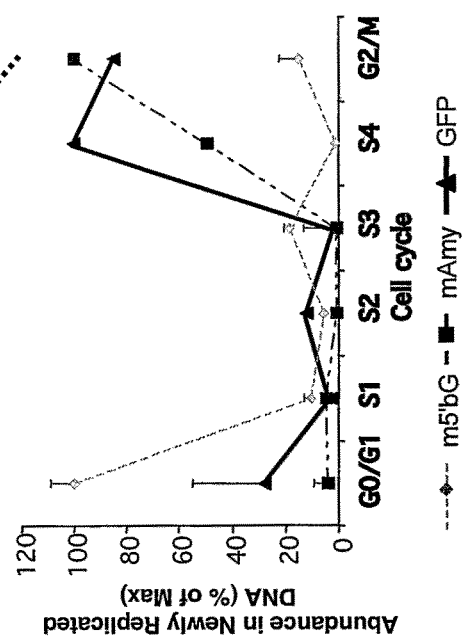
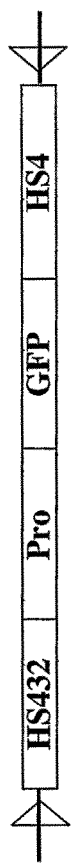
FIG. 2A
*Insertion into the late-replicating orientation*
FIG. 2B

SEQUENCE LISTING

<160> NUMBER OF SEQ ID NOS: 38

<210> SEQ ID NO 1
<211> LENGTH: 4680
<212> TYPE: DNA
<213> ORGANISM: Homo sapiens

<400> SEQUENCE: 1

```
ggatccatag ttcatcattt aaaaagaaa acaaaataga aaaaggaaaa ctatttctga      60
gcataagaag ttgtagggta agtctttaag aaggtgacaa tttctgccaa tcaggatttc     120
aaagctcttg ctttgacaat tttggtcttt cagaatacta taaatataac ctatattata    180
atttcataaa gtctgtgcat tttctttgac ccaggatatt tgcaaaagac atattcaaac    240
ttccgcagaa cactttattt cacatataca tgcctcttat atcagggatg tgaaacaggg    300
tcttgaaaac tgtctaaatc taaaacaatg ctaatgcagg tttaaattta ataaaataaa    360
atccaaaatc taacagccaa gtcaaatctg tatgttttaa catttaaaat attttaaaga    420 cgtctttttcc caggattcaa catgtgaaat cttttctcag ggatacacgt gtgcctagat    480
cctcattgct ttagttttt acagaggaat gaatataaaa agaaaatact taaattttat     540
ccctcttacc tctataatca tacataggca taatttttta acctaggctc cagatagcca    600
tagaagaacc aaacactttc tgcgtgtgtg agaataatca gagtgagatt ttttcacaag    660
tacctgatga gggttgagac aggtagaaaa agtgagagat ctctatttat ttagcaataa    720
tagagaaagc atttaagaga ataaagcaat ggaataagaa aatttgtaaa tttccttctg    780
ataactagaa atagaggatc cagtttcttt tggttaacct aaattttatt tcattttatt    840
gttttatttt atttttatttt atttttatttt gtgtaatcgt agtttcagag tgttagagct    900
gaaaggaaga agtaggagaa acatgcaaag taaaagtata acactttcct tactaaaccg    960
```

```
actgggtttc caggtagggg caggattcag gatgactgac agggccctta gggaacactg    1020
agaccctacg ctgacctcat aaatgcttgc tacctttgct gttttaatta catcttttaa    1080
tagcaggaag cagaactctg cacttcaaaa gttttcctc acctgaggag ttaatttagt    1140 acaagggaa aaagtacagg gggatgggag aaaggcgatc acgttgggaa gctatagaga    1200
aagaagagta aattttagta aaggaggttt aaacaaacaa aatataaaga gaataggaa    1260 cttgaatcaa ggaaatgatt ttaaaacgca gtattcttag tggactagag gaaaaaaata    1320
atctgagcca agtagaagac cttttcccct cctaccccta cttctaagt cacagaggct    1380 ttttgttccc ccagacactc ttgcagatta gtccaggcag aaacagttag atgtccccag    1440
ttaacctcct atttgacacc actgattacc ccattgatag tcacactttg ggttgtaagt    1500 gacttttat ttatttgtat ttttgactgc attaagaggt ctctagtttt ttatctcttg    1560
tttcccaaaa cctaataagt aactaatgca cagagcacat tgatttgtat ttattctatt    1620
tttagacata atttattagc atgcatgagc aaattaagaa aaacaacaac aaatgaatgc    1680
atatatatgt atatgtatgt gtgtatatat acacatatat atatatattt ttttcttt    1740 cttaccagaa ggttttaatc caaataagga gaagatatgc ttagaactga ggtagagttt    1800
tcatccattc tgtcctgtaa gtattttgca tattctggag acgcaggaag agatccatct    1860
acatatccca aagctgaatt atggtagaca aagctcttcc acttttagtg catcaatttc    1920
ttatttgtgt aataagaaaa ttgggaaaac gatcttcaat atgcttacca agctgtgatt    1980
ccaaatatta cgtaaataca cttgcaaagg aggatgtttt tagtagcaat ttgtactgat    2040
ggtatggggc caagagatat atcttagagg gagggctgag ggtttgaagt ccaactccta    2100
agccagtgcc agaagagcca aggacaggta cggctgtcat cacttagacc tcaccctgtg    2160
gagccacacc ctagggttgg ccaatctact cccaggagca gggagggcag gagccagggc    2220
tgggcataaa agtcagggca gagccatcta ttgcttacat ttgcttctga cacaactgtg    2280
ttcactagca acctcaaaca gacaccatgg tgcacctgac tcctgaggag aagtctgccg    2340
ttactgccct gtggggcaag gtgaacgtgg atgaagttgg tggtgaggcc ctgggcaggt    2400
tggtatcaag gttacaagac aggtttaagg agaccaatag aaactgggca tgtggagaca    2460
gagaagactc ttgggtttct gataggcact gactctctct gcctattggt ctattttccc    2520
acccttaggc tgctggtggt ctaccccttgg acccagaggt tctttgagtc ctttggggat    2580
ctgtccactc ctgatgctgt tatgggcaac cctaaggtga aggctcatgg caagaaagtg    2640
ctcggtgcct ttagtgatgg cctggctcac ctggacaacc tcaagggcac ctttgccaca    2700
ctgagtgagc tgcactgtga caagctgcac gtggatcctg agaacttcag ggtgagtcta    2760 tgggacccctt gatgttttct ttccccttct tttctatggt taagttcatg tcataggaag    2820
gggagaagta acagggtaca gtttagaatg ggaaacagac gaatgattgc atcagtgtgg    2880
aagtctcagg atcgttttag tttcttttat ttgctgttca taacaattgt tttcttttgt    2940
ttaattcttg ctttcttttt ttttcttctc cgcaattttt actattatac ttaatgcctt    3000
aacattgtgt ataacaaaag gaaatatctc tgagatacat taagtaactt aaaaaaaaac    3060
tttacacagt ctgcctagta cattactatt tggaatatat gtgtgcttat ttgcatattc    3120
ataatctccc tactttattt tcttttattt ttaattgata cataatcatt atacatattt    3180
atgggttaaa gtgtaatgtt ttaatatgtg tacacatatt gaccaaatca gggtaatttt    3240
gcatttgtaa tttaaaaaaa tgctttcttc ttttaatata cttttttgtt tatcttattt    3300
ctaatacttt ccctaatctc tttctttcag ggcaataatg atacaatgta tcatgcctct    3360
```

```
ttgcaccatt ctaaagaata acagtgataa tttctgggtt aaggcaatag caatatttct   3420
gcatataaat atttctgcat ataaattgta actgatgtaa gaggtttcat attgctaata   3480
gcagctacaa tccagctacc attctgcttt tattttatgg ttgggataag gctggattat   3540
tctgagtcca agctaggccc ttttgctaat catgttcata cctcttatct tcctcccaca   3600
gctcctgggc aacgtgctgg tctgtgtgct ggcccatcac tttggcaaag aattcacccc   3660
accagtgcag gctgcctatc agaaagtggt ggctggtgtg gctaatgccc tggcccacaa   3720
gtatcactaa gctcgctttc ttgctgtcca atttctatta aaggttcctt tgttccctaa   3780
gtccaactac taaactgggg gatattatga agggccttga gcatctggat tctgcctaat   3840
aaaaaacatt tattttcatt gcaatgatgt atttaaatta tttctgaata ttttactaaa   3900
aagggaatgt gggaggtcag tgcatttaaa acataaagaa atgaagagct agttcaaacc   3960
ttgggaaaat acactatatc ttaaactcca tgaaagaagg tgaggctgca aacagctaat   4020
gcacattggc aacagccctg atgcctatgc cttattcatc cctcagaaaa ggattcaagt   4080
agaggcttga tttggaggtt aaagttttgc tatgctgtat tttacattac ttattgtttt   4140
agctgtcctc atgaatgtct tttcactacc catttgctta tcctgcatct ctcagccttg   4200
actccactca gttctcttgc ttagagatac caccttttccc ctgaagtgtt ccttccatgt   4260
tttacggcga gatggtttct cctcgcctgg ccactcagcc ttagttgtct ctgttgtctt   4320
atagaggtct acttgaagaa ggaaaaacag ggggcatggt ttgactgtcc tgtgagccct   4380
tcttccctgc ctcccccact cacagtgacc cggaatctgc agtgctagtc tcccggaact   4440
atcactcttt cacagtctgc tttggaagga ctgggcttag tatgaaaagt taggactgag   4500
aagaatttga aaggggggctt tttgtagctt gatattcact actgtcttat taccctatca   4560
taggcccacc ccaaatggaa gtcccattct tcctcaggat gtttaagatt agcattcagg   4620
aagagatcag aggtctgctg gctcccttat catgtccctt atggtgcttc tggctctgca   4680
```

<210> SEQ ID NO 2
<211> LENGTH: 2371
<212> TYPE: DNA
<213> ORGANISM: Homo sapiens

<400> SEQUENCE: 2

```
atggtgcacc tgactcctga ggagaagtct gccgttactg ccctgtgggg caaggtgaac     60
gtggatgaag ttggtggtga ggccctgggc aggttggtat caaggttaca agacaggttt    120
aaggagacca taggaaactg gcatgtggag acagagaag actcttgggt ttctgatagg    180
cactgactct ctctgcctat tggtctattt tcccaccctt aggctgctgg tggtctaccc    240
ttggacccag aggttctttg agtcctttgg ggatctgtcc actcctgatg ctgttatggg    300
caaccctaag gtgaaggctc atggcaagaa agtgctcggt gcctttagtg atggcctggc    360
tcacctggac aacctcaagg gcacctttgc cacactgagt gagctgcact gtgacaagct    420
gcacgtggat cctgagaact tcagggtgag tctatgggac ccttgatgtt ttctttcccc    480
ttcttttcta tggttaagtt catgtcatag gaagggggaga agtaacaggg tacagtttag    540
aatgggaaac agacgaatga ttgcatcagt gtggaagtct caggatcgtt ttagtttctt    600
ttatttgctg tcataacaa ttgttttctt tgtttaatt cttgctttct ttttttttct    660
tctccgcaat ttttactatt atacttaatg ccttaacatt gtgtataaca aaaggaaata    720
tctctgagat acattaagta acttaaaaaa aaactttaca cagtctgcct agtacattac    780
tatttggaat atatgtgtgc ttatttgcat attcataatc tccctacttt attttctttt    840
```

```
attttaatt gatacataat cattatacat atttatgggt taaagtgtaa tgttttaata      900
tgtgtacaca tattgaccaa atcagggtaa ttttgcattt gtaattttaa aaaatgctttt    960 cttcttttaa tatactttt tgtttatctt atttctaata cttccctaa tctctttctt      1020 tcagggcaat aatgatacaa tgtatcatgc ctctttgcac cattctaaag aataacagtg    1080
ataatttctg ggttaaggca atagcaatat ttctgcatat aaatatttct gcatataaat    1140
tgtaactgat gtaagaggtt tcatattgct aatagcagct acaatccagc taccattctg    1200 ctttatttt atggttggga taaggctgga ttattctgag tccaagctag gccttttgc     1260 taatcatgtt catacctctt atcttcctcc cacagctcct gggcaacgtg ctggtctgtg    1320
tgctggccca tcactttggc aaagaattca ccccaccagt gcaggctgcc tatcagaaag    1380
tggtggctgg tgtggctaat gccctggccc acaagtatca ctaagctcgc tttcttgctg    1440
tccaatttct attaaaggtt cctttgttcc ctaagtccaa ctactaaact ggggatatt     1500 atgaagggcc ttgagcatct ggattctgcc taataaaaaa catttatttt cattgcaatg    1560
atgtatttaa attatttctg aatatttac taaaaaggga atgtgggagg tcagtgcatt    1620
taaaacataa agaaatgaag agctagttca aaccttggga aaatacacta tatcttaaac    1680
tccatgaaag aaggtgaggc tgcaaacagc taatgcacat tggcaacagc cctgatgcct    1740
atgccttatt catccctcag aaaaggattc aagtagaggc ttgatttgga ggttaaagtt    1800
ttgctatgct gtattttaca ttacttattg ttttagctgt cctcatgaat gtcttttcac    1860
tacccatttg cttatcctgc atctctcagc cttgactcca ctcagttctc ttgcttagag    1920
ataccacctt tcccctgaag tgttccttcc atgttttacg gcgagatggt ttctcctcgc    1980
ctggccactc agccttagtt gtctctgttg tcttatagag gtctacttga agaaggaaaa    2040 acaggggggca tggtttgact gtcctgtgag cccttcttcc ctgcctcccc cactcacagt     2100
gacccggaat ctgcagtgct agtctcccgg aactatcact ctttcacagt ctgctttgga    2160
aggactgggc ttagtatgaa aagttaggac tgagaagaat ttgaaagggg cttttttgta    2220
gcttgatatt cactactgtc ttattaccct atcataggcc caccccaaat ggaagtccca    2280
ttcttcctca ggatgtttaa gattagcatt caggaagaga tcagaggtct gctggctccc    2340
ttatcatgtc ccttatggtg cttctggctc t                                    2371
```

<210> SEQ ID NO 3
<211> LENGTH: 2306
<212> TYPE: DNA
<213> ORGANISM: Homo sapiens
<400> SEQUENCE: 3

```
gatccatagt tcatcattta aaaagaaaa caaaatagaa aaaggaaaac tatttctgag       60
cataagaagt tgtagggtaa gtctttaaga aggtgacaat ttctgccaat caggatttca    120
aagctcttgc tttgacaatt ttggtctttc agaatactat aaatataacc tatattataa    180
tttcataaag tctgtgcatt ttctttgacc caggatattt gcaaagaca tattcaaact      240 tccgcagaac actttatttc acatatacat gcctcttata tcagggatgt gaaacagggt    300
cttgaaaact gtctaaatct aaaacaatgc taatgcaggt ttaaatttaa taaaataaaa    360
tccaaaatct aacagccaag tcaaatctgt atgttttaac attaaaaata ttttaaagac    420
gtcttttccc aggattcaac atgtgaaatc ttttctcagg gatacacgtg tgcctagatc    480
ctcattgctt tagttttta cagaggaatg aatataaaaa gaaatacttt aaattttatc    540
cctcttacct ctataatcat acataggcat aatttttaa cctaggctcc agatagccat    600
```

| | | |
|---|---|---|
| agaagaacca aacactttct gcgtgtgtga gaataatcag agtgagattt tttcacaagt | 660 | |
| acctgatgag ggttgagaca ggtagaaaaa gtgagagatc tctatttatt tagcaataat | 720 | |
| agagaaagca tttaagagaa taaagcaatg gaaataagaa atttgtaaat ttccttctga | 780 | |
| taactagaaa tagaggatcc agtttctttt ggttaaccta aattttattt cattttattg | 840 | |
| ttttatttta ttttatttta ttttatttg tgtaatcgta gtttcagagt gttagagctg | 900 | |
| aaaggaagaa gtaggagaaa catgcaaagt aaaagtataa cactttcctt actaaaccga | 960 | |
| ctgggtttcc aggtaggggc aggattcagg atgactgaca gggcccttag ggaacactga | 1020 | |
| gaccctacgc tgacctcata aatgcttgct acctttgctg ttttaattac atcttttaat | 1080 | |
| agcaggaagc agaactctgc acttcaaaag ttttcctca cctgaggagt taatttagta | 1140 | |
| caaggggaaa aagtacaggg ggatggggaga aaggcgatca cgttgggaag ctatagagaa | 1200 | |
| agaagagtaa attttagtaa aggaggttta acaaacaaa atataaagag aaataggaac | 1260 | |
| ttgaatcaag gaaatgattt taaaacgcag tattcttagt ggactagagg aaaaaaataa | 1320 | |
| tctgagccaa gtagaagacc ttttcccctc ctaccctac tttctaagtc acagaggctt | 1380 | |
| tttgttcccc cagacactct tgcagattag tccaggcaga aacagttaga tgtccccagt | 1440 | |
| taacctccta tttgacacca ctgattaccc cattgatagt cacactttgg gttgtaagtg | 1500 | |
| acttttatt tatttgtatt tttgactgca ttaagaggtc tctagttttt tatctcttgt | 1560 | |
| ttcccaaaac ctaataagta actaatgcac agagcacatt gatttgtatt tattctattt | 1620 | |
| ttagacataa tttattagca tgcatgagca aattaagaaa acaacaaca aatgaatgca | 1680 | |
| tatatatgta tatgtatgtg tgtatatata cacatatata tatatttt ttttcttttc | 1740 | |
| ttaccagaag gttttaatcc aaataaggag aagatatgct tagaactgag gtagagtttt | 1800 | |
| catccattct gtcctgtaag tatttgcat attctggaga cgcaggaaga gatccatcta | 1860 | |
| catatcccaa agctgaatta tggtagacaa agctcttcca cttttagtgc atcaatttct | 1920 | |
| tatttgtgta ataagaaaat tgggaaaacg atcttcaata tgcttaccaa gctgtgattc | 1980 | |
| caaatattac gtaaatacac ttgcaaagga ggatgttttt agtagcaatt tgtactgatg | 2040 | |
| gtatggggcc aagagatata tcttagaggg agggctgagg gtttgaagtc caactcctaa | 2100 | |
| gccagtgcca aagagccaa ggacaggtac ggctgtcatc acttagacct caccctgtgg | 2160 | |
| agccacaccc tagggttggc caatctactc ccaggagcag ggagggcagg agccagggct | 2220 | |
| gggcataaaa gtcagggcag agccatctat tgcttacatt tgcttctgac acaactgtgt | 2280 | |
| tcactagcaa cctcaaacag acacca | 2306 | |

<210> SEQ ID NO 4
<211> LENGTH: 1320
<212> TYPE: DNA
<213> ORGANISM: Homo sapiens

<400> SEQUENCE: 4

| | | |
|---|---|---|
| cctgtcctca tgccagcggc tttggctggg gttggtctga agcctgcacg cggcagttct | 60 | |
| ttgttaaaga tctgagggac tcgtcagtcc tagcgtcgcc gcctgcagcc tcttccaagc | 120 | |
| cctgcgtcca gcgagcgtca cagcacaacc tgcaaaaacg gagctgggct gcagctgggg | 180 | |
| ctggcatgga ctttcatttc agagattcgg ttttaagaa gatgcatgcc tagcgtgttc | 240 | |
| ttttttttt ccaatgattt gtaatataca ttttatgact ggaaactttt ttgtacaaca | 300 | |
| ctccaataaa cattttgatt ttaggttctg cctctgagtt tattcctgag gggaagctcg | 360 | |
| agccgggcct ctgccctaat gaagcggatg tctaagaaag atccctccac ccccaaggaa | 420 | |

```
aaaggtcact ggctagtgta gctagtgtaa acaggaccca ggcgatgcat gggaccctgc        480 ccttttttt  ctagtgagcc tccgacgctg ttgcacaagc tgactcttcg tcacgtgatg        540
cgaccggctc cgccccggcg gcaacacgct gtatagacgc gccgggtgcc tcgtgcgcat        600
gcgcggcagg cccttcggga cgagctggag gcagagcgtg agtacaaagt gatcggcctc        660
ggccgacgca gtagcccccc tactccccgg ccaagtcagg gcctccctct tccgcggag         720 tcgcaaccac gggtagctcg tgtaggtaac ggcaggtcca ggcctccgca tgagcggagg        780
gccccccgca cgaccttgaa tggcccggtg gcgcgcgcgg tcgtgtggga gttgtagtcc        840
tccgtccccg tccgcgcgga ctccgtttcc cgtggtgccc cgggcggccc gcttccggcg        900
cagttagtta cgagtcggcg cacgcggcct cggtccggtt gactttgcgg agccatggag        960
ggcggcttcg gctccgattt cggggctcc  ggcagcggga agctggaccc agggctcata       1020
atggagcagg tgaaagtgca gatcgccgtg gccaacgcgc aggagctgct gcaggtgcgg       1080
ggctggccgg ggacgggcgc tggggcgac  agggccaccc ctaggggccg acgtcgcggc       1140
taagcctcgc gtgtctccac agaggatgac ggacaagtgt ttccggaagt gtatagggaa       1200
acctaggggc tccctagaca actccgagca ggtgagaccc gcggaaggtt cggggcaagg       1260
gtcgcgaggg cctagattcg ggggggaggt gtctgcgcgt gcgagacaac ggggaggtgc       1320

<210> SEQ ID NO 5
<211> LENGTH: 2400
<212> TYPE: DNA
<213> ORGANISM: Homo sapiens

<400> SEQUENCE: 5
agcttgtttg gccgttttag ggtttgttgg aattttttt  tcgtctatgt acttgtgaat         60
tatttcacgt ttgccattac cggttctcca tagggtgatg ttcattagca gtggtgatag        120
gttaattttc accatctctt atgcggttga atagtcacct ctgaaccact ttttcctcca        180
gtaactcctc tttcttcgga ccttctgcag ccaacctgaa agaataacaa ggaggtggct        240
ggaaacttgt tttaaggaac cgcctgtcct tcccccgctg gaaaccttgc acctcggacg        300
ctcctgctcc tgccccacc  tgaccccgc  cctcgttgac atccaggcgc gatgatctct        360
gctgccagta gagggcacac ttactttact ttcgcaaacc tgaacgcggg tgctgcccag        420 agaggggcg  gagggaaaga cgctttgcag caaaatccag catagcgatt ggttgctccc        480
cgcgtttgcg gcaaaggcct ggaggcagga gtaatttgca atccttaaag ctgaattgtg        540
cagtgcatcg gatttggaag ctactatatt cacttaacac ttgaacgctg agctgcaaac        600
tcaacgggta ataacccatc ttgaacagcg tacatgctat acacacaccc ctttcccccg        660
aattgttttc tcttttggag gtggtggagg gagagaaaag tttacttaaa atgcctttgg        720
gtgagggacc aaggatgaga agaatgtttt ttgttttttca tgccgtggaa taacacaaaa        780
taaaaaatcc cgagggaata tacattatat attaaatata gatcatttca gggagcaaac        840
aaatcatgtg tggggctggg caactagctg agtcgaagcg taaataaaat gtgaatacac        900
gtttgcgggt tacatacagt gcactttcac tagtattcag aaaaaattgt gagtcagtga        960
actaggaaat taatgcctgg aaggcagcca aattttaatt agctcaagac tccccccccc       1020
ccccaaaaaa aggcacggaa gtaatactcc tctcctcttc tttgatcaga atcgatgcat       1080
tttttgtgca tgaccgcatt tccaataata aaaggggaaa gaggacctgg aaaggaatta       1140
aacgtccggt ttgtcggggg aggaaagagt taacggtttt tttcacaagg gtctctgctg       1200
actcccccgg ctcggtccac aagctctcca cttgccccct ttaggaagtc cggtcccgcg       1260
```

```
gttcgggtac cccctgcccc tcccatattc tcccgtctag cacctttgat ttctcccaaa   1320
cccggcagcc cgagactgtt gcaaaccggc gccacagggc gcaaagggga tttgtctctt   1380
ctgaaacctg gctgagaaat tgggaactcc gtgtgggagg cgtgggggtg ggacggtggg   1440
gtacagactg gcagagagca ggcaacctcc ctctcgccct agcccagctc tggaacaggc   1500
agacacatct cagggctaaa cagacgcctc ccgcacgggg ccccacggaa gcctgagcag   1560
gcggggcagg aggggcggta tctgctgctt tggcagcaaa ttgggggact cagtctgggt   1620
ggaaggtatc caatccagat agctgtgcat acataatgca taatacatga ctcccccaa    1680
caaatgcaat gggagtttat tcataacgcg ctctccaagt atacgtggca atgcgttgct   1740
gggttatttt aatcattcta ggcatcgttt tcctccttat gcctctatca ttcctcccta   1800
tctacactaa catcccacgc tctgaacgcg cgcccattaa tacccttctt tcctccactc   1860
tccctgggac tcttgatcaa agcgcggccc ttccccagc cttagcgagg cgccctgcag   1920
cctggtacgc gcgtggcgtg gcggtgggcg cgcagtgcgt tctctgtgtg gagggcagct   1980
gttccgcctg cgatgattta tactcacagg acaaggatgc ggtttgtcaa acagtactgc   2040
tacggaggag cagcagagaa agggagaggg tttgagaggg agcaaaagaa aatggtaggc   2100
gcgcgtagtt aattcatgcg gctctcttac tctgtttaca tcctagagct agagtgctcg   2160
gctgcccggc tgagtctcct ccccaccttc ccaccctcc ccaccctccc cataagcgcc    2220
cctcccgggt tcccaaagca gagggcgtgg gggaaaagaa aaaagatcct ctctcgctaa   2280
tctccgccca ccggcccttt ataatgcgag ggtctggacg gctgaggacc cccgagctgt   2340
gctgctcgcg gccgccaccg ccgggcccg gccgtccctg ctcccctcc tgcctcgaga     2400

<210> SEQ ID NO 6
<211> LENGTH: 5794
<212> TYPE: DNA
<213> ORGANISM: Cricetulus griseus

<400> SEQUENCE: 6
ggatcctcct agctcggagt cagcaaggaa ctgaagccct taattttata gacacaaagg     60
aatccattgt gtggctcctt cccagccaag tctcagatga gtcacagacc tgcatggcac    120
cttatgcagt cttttgaggt cccaagaata ggatgcagat aagccatgcc agaatcccaa    180
cacacaaagc cttagtgata tagtaaatat gtattgtgtc taggctgctg catttctggt    240
tatgctactg tgcagtaata cacaactaat acagatgtga tggttaatat tatgtgacaa    300
cttgagtggg gcacagaggt acagacactt ggtaaaccat tctgggtgcc acgtaaggat    360
agttttggat gacataaaca tttagattag tatgctgggt aaaatacatt gtccatccca    420
atggcatggc ctttgtccaa ctagatgaca gctggaatag aaaagtctgc ctctctcata    480
gttctcaggc ctttgagctc agactagaca gaactcacag gttctctgag ctttccagct    540
tgatgaatgt ccatggcagt cttcacactt aacacctgac agacttaatg atcatatgaa    600
ccaattcaaa tctgaccatc actcgggtca ttcttttgat tctgtcactt tggagaacta    660
ataccgagga cataaaatgc catcacatcg ttattttctt cctgtctgtg aatattttc     720
ttttttttct tgtttttttt tttttttttt tttttttttt ttttttttg gttttttctct    780
gtgtagcttt ggagcctatc ctggcacttg ctctggagac caggctgacc tgaactctca    840
gagaaccgcc tgcctctgcc tcccgagtgc tgggattaaa ggcgtgtacc accaacgctc    900
gggcctgtct gtgaatattt aaaatgaaaa ctttggaaat gttctgaaac cagctggtgt    960
cagatagtca gagaactttc gtaaggtagg tgtgggttat agcataatcc cacacaagag   1020
```

```
gctgaagcag gaggattttg tgtttgaggg cagctagagc cacatggtga gtccctgcct      1080
caaaacacaa aagcaagaca aaaacaagct ccaaataaga ttcactgggc cctttctttc      1140
cttccttctc agtgagtcca cttgctttaa aatcaggtct taaagacgca ctagatgctg      1200
aacttaacag taataataaa tatcttctct tacagtacag attatgctct ataaacactg      1260
cactgataaa gttcagcctt aacctttgtt ctgtaaatgt ttcctagttt ttctactgcc      1320
gtattataag acaaatgtca gcatgaaggc aggttttttca gaaaacacag cagctccaca     1380
gatggcctct aatccataat cattaaagac aagactgcaa cttttcaac tggaaatcat       1440 tcaagatgtt tttctgaagt ccctaccagg acacaagcca ccctggttgc tgtgtgacat      1500
cagttaggta gactctgaac tggcttccca agaaattata caaaagcaag gtgtcaccta      1560
gtattagcat aacttctgat aactactgtc ttagctgggg tttctattgc tgtgaagaga     1620
caccatgacc acagaaactc ttataaagga aagcaattat tgggtccagc ttacagttca     1680
gaggtttaat ccattgtcat gattgcagga agtatggtgc gccacaggca gacatggtgc     1740
tggagaagta gatgagagtt ctatatcaga ttgacacact tcttccaaca aggccacacc     1800
tccactcact ctgagcctat ggggccattt tcattcaaac caccaaagct acaaggtagc     1860 ttataccccca gcttgctatt tctgatgaga cttagtaaat agtcttaaaa gcccataaaa    1920
tgactcaaaa ctagttttttt tattattatt attagttcaa attaggaaga agcttgcttt    1980
acatgtcaat cccttctccc tctccctcat caaaactagt tttttgtttt ttaggttttt     2040
tttcaagaca gggtttctct gtgtagcttt ggagcctatc ctggcactcg ctctggagac     2100
caggctggcc tcgaactcac agagatctgc ctgcctttgc ctcccgagtc ctgggattaa     2160
aggcatgcac caccaacacc tggccaaaat tagttttaag ttccagttct aggagcctcc     2220
aatgccctct tttggcttcc atgggaacca ggaacactat atatatatat atatatatat    2280
atatatatat atatatatat atattcaggc aaatatttat gcataaaaa ataaaataaa      2340 tcttttttcc tttttttttt aaagaagtgc aattgtcttg gaattttgt ggctgctctg      2400 cccttatgtg taactggaca ctaccagcat ctaaacactg gcctgaaacc agccaaagaa     2460
aacctttgtg ccaggtcctg tgtcaaagta ttatgttcct tttaggatat cctatatcgt     2520
aaaggattta ttttactgat agcatcttaa cttcctttga aaggttggtc ttctcaagca     2580
gtcctcgtgg agctggctcc tcagctaatg ccaggggaca ataatgatcc cctcccaaaa     2640
ccaaacagaa aaccatggca actctggttt ccttgggcag cacctgcttt aagaatgagc     2700 aaaatgaccaa tcagctcatg aaactaaata ctctattatt actaaaatat ttttttgaga    2760
cagggcatgg aattcatcac atagttcagg ttggccttga actcagagag actcacttac     2820
ctttgcctcc cacgtgctgg aattaaaggc atgaaccacc acaccaaaca taacacttga     2880
attttggaag agtccttctt ccaatagatt tgaggttttg aaaatgtggc acagaaaata     2940
tgaattcaaa tataatgaaa acaagagata actttcaact aagtttctat aggttcttgc     3000
taggaatcct aagcttgtct gaaactctag agcttctgtt tctagtcttc tgagtgttag     3060
tattgtaggt atgtgccctg cctcagtgtg atgtttttga taatcttaaa gaaatcaaag     3120
aaattttata aaagactaga ctgtgctaca caaaaagaat attcagatgc caagaaagag     3180
ttcttagaaa ttaagaaata tgctactagt ataaatcctt tataaagtgg aatgacaaat     3240
ctgatgaaat cttactaaaa gtagaaaaac ataaacatca aagacatgaa taataagaaa     3300
atcatattgt gcatatcatt aacctaaaac attaacttgc aaaaatagaa tagtccaaaa     3360
agtaaacaaa ataaataaat caccaagaca tgatacaagg acaattccta gaatgataaa     3420
```

```
acaagaatat tcattataaa aggccctatc actaaagcac aacagaaaca gactcaaaag    3480
ataaatcttc attgtcactg gagagaagtc atactatcat agcactcaga aggaaataaa    3540
aatcaaaatg tcaaaaagga cctcagcctc tgaaacacaa atacaaaata tgtccgcctt    3600
cttgacaggc attactcttc aattaacatt ttaagaaaac tataaagaga gcttagtatt    3660
ttaagaaatc tgtagctatt tcttttataa gcatgacaac taagtttcct gatttaaaca    3720
gacctaaaaa accggtgaag tgagtggaga aaggggatac gaagacagca tcccacatga    3780
ctgctcccag taaaggcaag gtcttcatcc attttatcct gaactctggg aaatttataa    3840
agaacagaaa tgtatttctc tcagttctgg agcctcagtc caggacacta agtctaggta    3900
ctacactctc acatggtgga aactagaaag caagctcact tgtcactcac tacctgatgc    3960
ctctttcatc aatcccattg ataaggaaga gacctggcat ctcagtttcc taaggactca    4020
gctcttacta acattagctg tcatttctgg gtcactgcaa cagaaagcct gacagaagca    4080
acccaggggg agaaggatgt attttggctc actgtctctg aggatttcaa cttatcccag    4140
caataaaggg ataaaggcat tgcagcagga atatgtgtgg cagaagctgt ttatgtcaca    4200
ataaacaaat aaacacacgc tagcgcgcgc gcacacacac acacacacac acacacacac    4260
acacacacag agagagagag agagagagag agagagagag agagagagag ggggggggc    4320 agacagacag acagagggag agaggcagag agggagagag agagagagag agagagagag    4380
agagagagag agagagagag agagagagaa atcaaaggcc cacctccatc agactggtcc    4440
catatcccaa atttctagaa cctcctaaaa caacaccatc aactgaggga gacattttg    4500 gattgaaagc ataatgccat tacccaggca gaatctgcct gtctggggga gtcacattta    4560
agccatggta tcaattgacc tcatgtaatt tcagaatact acataaaact atcagatatt    4620
tttcatgatg aatttctaaa gcttgaaatt ccctttgaat aaaggaccaa ctacagaatt    4680
ttgctgagtc tacaattaca tacatgaaaa tgtaactacg aagtggccag ccacaatgaa    4740
aattaaagtg tttgggtggt ctgtctctat tgatgctctt ctttgccctg ttttttttta    4800
atattgttga tggtttgttt ttcttttaag atacttggcc ccaagaaaaa aaatgacagc    4860
cttaattaat tttgttttact ctcctgacag ttttaaaaga caaatttatg aagacctgac    4920
tgttccatgt agtattagaa agatgtaaaa ttaagggttg cttaagctgc gtgtagaatt    4980
gaagagcaca gcatttgagt gacagggtac aattagagat catcagggat gtggcacaaa    5040
ggtgtactca acctcacctt ttcctgctta gcagagaaca gggtgcctcg gtgagatagg    5100
aaattaatca aatagaagaa gaaatagtaa ttttagaagg atcaaatttt ctggttagaa    5160
tgatcaaaac tacaagactg taactaaaat atagtcaaac ccattttcaa ctggaatctg    5220
tgctatttca tgtatagatt aactagaatc taattttaa attttcatct tacttccaaa    5280
aatatttgtc caaatactct gtgaatgcat tagtttctta tgggaaaaca tcatatcttt    5340
tgatcaatgt gttcttagc ttgaggttct ctccaaacag gaccaagacg aggccaggac    5400
caatgtgata caacccatag tcctcaagaa atagttgtca tttcttattc caattgcatc    5460
ccaaggtctc atctcatttt gcgtgtgcct ttgacacccc ataccacat aaactaaggt    5520 ggtgttattt tttgaggccc tgaaggtatc ttcaggaatc cataagtgag ccttaagctg    5580 catctgata taggaatctg aaagtgtccc ttctctgcat gatctcttct ttcagttttt    5640
caagtcagtg tgccacagga atcaggaacg ataaatggag aggggaagtg cagttgcttg    5700
gtatagacac cccagaggct attgcatcc tgtccttcaa aatctctctg agccttcctg    5760
cctaagcctt gttttgagtt gggtttgtgg tacc                               5794
```

<210> SEQ ID NO 7
<211> LENGTH: 3850
<212> TYPE: DNA
<213> ORGANISM: Drosophila melanogaster

<400> SEQUENCE: 7

| | | | | | |
|---|---|---|---|---|---|
| tatatacaaa | cgtacatgtt | gaaaacagcg | agaaaataaa | tcgagaataa | cattttaaat | 60 |
| taatataata | acaatcggaa | ggacttggtc | ctcgcaatca | cagtggcgca | cgcgataagc | 120 |
| caagtatctc | aagaacgttc | accaattaag | agaacctccc | aatcgtgcac | atagaaaaat | 180 |
| atccatatgt | ataaaataac | aataattaag | aacctgcgtt | gttaattctt | ttatctgaaa | 240 |
| accccgttcg | ccggctgcat | gtaaatggat | aatccagaag | ccaacatgga | agagtcaaac | 300 |
| ccaaattacg | atgttaacca | aagactacaa | aagccgaggg | ttggccgca | cgtcaatgag | 360 |
| ttccatccct | ccatgatgta | tccggatgat | cccaggcggt | acttccacaa | tgcctccaca | 420 |
| gacccacagc | accagccaca | gcaacatccg | cagcagcagc | cagagcagca | tccggagcag | 480 |
| catccgcagc | atccgctgca | ttcgcagcaa | cagccgcagc | aacatccaca | gcaacagccg | 540 |
| cagcaacatc | cacagcaaca | gacgcagcaa | ccgccacagc | tgcagccgca | acaacatcca | 600 |
| caggcacaga | tacagcctcc | cattcccgta | cccatatcca | cacccatgga | agggactatg | 660 |
| gaagttcccg | ttaagatgcc | agaatactgc | cccgagacaa | gccagcccgt | cgagcctgac | 720 |
| cgggtcatta | atcccttggc | cgaggtagcc | aaaaacacag | taccttatgg | ccacaagcgc | 780 |
| aagaactcgg | cgggagagga | ccaggcggca | aacaagaaac | tcagtatggc | ggccgccgag | 840 |
| gagaagaaga | acagtcacct | gcggaagaac | atccgcgacg | tgatgaacga | aacaatctg | 900 |
| gacacaacca | cgctggcggc | ccagcagagg | gaatcggaac | gcttggctcg | cgttgctggt | 960 |
| caacagaagt | caatgcgcga | gatccagaag | caggtggtgc | acaagcagat | cttccgcatc | 1020 |
| ctgcagctgg | acgaaagcga | aggcatcgag | agctgtgccg | tggccaatcc | cgtcgagcac | 1080 |
| cacccgcccg | tcgactttcc | ggaggaggag | atcgcctcgg | acacgtttga | cgattcgaac | 1140 |
| agcagcagcc | tgagtggcgg | cagcattgag | gacgtcctgc | acaagggagc | cagcgtgcag | 1200 |
| cccagcgagg | tggtcacaat | agacgacagc | tccgacgacg | actgcatcct | tctctccgag | 1260 |
| gaggaggagg | aggaagatga | cgaggattta | aacgagtcgg | acgatgccac | caacagcggt | 1320 |
| atgcatgtca | agatatata | caatgttccc | gacgagaacg | gacaggtggt | ggtcaacatg | 1380 |
| gcgcatccgg | agggcgagga | gaccctgtac | ctggccccgc | agatagcgaa | agtgataaag | 1440 |
| ccgcaccaga | tcgcggcgt | ccgctttctg | tacgacaaca | tcatcgaatc | cacacggagg | 1500 |
| tacaacaaat | cgagcgggtt | cggctgcatt | ctggcccact | ccatgggcct | gggcaagacg | 1560 |
| ttgcaggttg | tttccttctg | tgatattttc | ctgagacata | cctcggcaaa | gacagtgtta | 1620 |
| tgtgtgatgc | ccatcaacac | gctgcagaat | tggctaagcg | agttcaacat | gtggattccg | 1680 |
| cgctactcga | cggacagcaa | tgttcgcccc | cgcaactttg | acatcttcgt | gctgaacgac | 1740 |
| cagcagaaga | cgctgacggc | tcgggcgaag | gtgatcctca | attgggtgca | cgatggaggt | 1800 |
| gtgctcctca | tcggctacga | gctgttccga | ctgctggctc | tcaagctggt | gaagacgcgc | 1860 |
| aagcgaaagg | gtagcgtcat | ccggcccgac | ggcatggact | ccagcagcga | tctcatgaat | 1920 |
| ctggtatacg | aggccttggt | gaagcccgga | cctgacctgg | taatctgcga | tgagggacac | 1980 |
| cggatcaaga | actcccacgc | cggcatctcg | ctggccctga | aggagatcag | gacgcggcgt | 2040 |
| cgcattgtgc | tcaccggcta | ccccttgcag | aacaatctgc | tcgagtactg | gtgcatggtg | 2100 |
| gactttgtgc | gacccaacta | cctgggcacc | cgcacggagt | tctgcaacat | gttcgagcgt | 2160 |

-continued

```
cccatccaga atggccagtg cgtggactcc acgcccgatg acatcaagct aatgcgctac    2220
agggcgcacg tgctgcactc cctgctgctg ggattcgttc agcggcgatc gcacactgtg    2280
ctgcagctga cgctgcctca gaagtacgag tatgtcatcc tggtcaaaat gaccgccttt    2340
cagcgcaagc tctacgacac cttcatgacg gatgtggtgc gcacaaaggc ctttccaaat    2400
ccgctgaagg cctttgctgt ttgctgtaaa atctggaacc atccagacgt tctgtataat    2460
tttctgaaaa aatgtgagac tgatttagat ttagaaatcg acgaggaggt taccaagggc    2520
gctgccacgc ccattgtgga gccaagtgca gattcttcct tgagtttggc atcgcctctc    2580
gagaagaaaa tcaatggatc cggggatccg atcaatagta tcgaaacgtt ttccaaagcc    2640
gagaatcaaa cattattcaa catccccgca tcatcggatt tgaatgctaa atatttgaac    2700
aagagtccaa gcttctacga cgaaaaacct gagccactta attatggatc tttcggcagt    2760
gaggggaaga caaactactg gatggattcc agtattctac ccaagccggg atgcgtggaa    2820
gtcattaagc aaacggacac gaacatgtcg agcaactttg aaagtattac ggggtcttcg    2880
gagatcgtgg atctggacac aaacgaaata aaaaccgtcg aaacgacgat acaagcgccg    2940
tgttccaaca atcaactgga taatgggtgc aacgctggca aaccaagtga atggaacgcc    3000
gcgggcagta aaaactcaag tggcgttgct gctgccgagc cgtttaaaaa gctactgaag    3060
agcaagcagc gaaacgaaga gttttcgtgt tcgtgggctg tggatttgat gaagaactac    3120
gtgtctggcc taatatcgaa ttcgcccaaa atggagatat tcttctgcat cctgaaagag    3180
agcctgaatt tgggagatcg tattctgttg tttagccaaa gtcttttaac cttaaatcta    3240
ctcgaagtct atctgaaatc tagttatgtt cctggtagca accaactttg gactaaaaac    3300
agctcttatt ttcgtttgga tggttctact tcctcgcagg aaagggaaag gctagtcaat    3360
gaatttaatg caaatagtaa tgttaagctt ttttttaatat caacaagagc cggctcattg    3420
gggataaacc tcaccggagc gaatcgcgtt ataatattcg atgctagttg gaatccctgt    3480
cacgatacac aagctgtata taggatttat agatacggtc agacaaagcc gtgctttgtg    3540
taccgaatcg taatggacag gtgtctggag aaaaagattt acgatcggca gatcaagaaa    3600
caaggaatgt ccgatagaat agtcgatgaa tgcaatcctg aggcgcatct ctccatgaag    3660
gatatcacaa atctgtgcca ggactacgac tctgatgaag acactgtcga ggaggtgaat    3720
aaatctacag gcgatttaag taagccaggc tcgccgtcgg aggaaggaag caagccagga    3780
agtgcaaata tgtcgccaaa cgcgtcgaat aaatcaaata atggacccac gaagccacta    3840
gacgatcaaa                                                          3850
```

<210> SEQ ID NO 8
<211> LENGTH: 18
<212> TYPE: DNA
<213> ORGANISM: Artificial sequence
<220> FEATURE:
<223> OTHER INFORMATION: oligonucleotide primer

<400> SEQUENCE: 8

```
tggaaaagca acccctgc                                                   18
```

<210> SEQ ID NO 9
<211> LENGTH: 21
<212> TYPE: DNA
<213> ORGANISM: Artificial sequence
<220> FEATURE:
<223> OTHER INFORMATION: oligonucleotide primer

<400> SEQUENCE: 9
acagaggctt tttgttcccc c                                              21

<210> SEQ ID NO 10
<211> LENGTH: 22
<212> TYPE: DNA
<213> ORGANISM: Artificial sequence
<220> FEATURE:
<223> OTHER INFORMATION: oligonucleotide primer

<400> SEQUENCE: 10
tgagggtttg aagtccaact cc                                             22

<210> SEQ ID NO 11
<211> LENGTH: 20
<212> TYPE: DNA
<213> ORGANISM: Artificial sequence
<220> FEATURE:
<223> OTHER INFORMATION: oligonucleotide primer

<400> SEQUENCE: 11
agcaaagacc ccaacgagaa                                                20

<210> SEQ ID NO 12
<211> LENGTH: 18
<212> TYPE: DNA
<213> ORGANISM: Artificial sequence
<220> FEATURE:
<223> OTHER INFORMATION: oligonucleotide primer

<400> SEQUENCE: 12
tccgtcccct tctcctcc                                                  18

<210> SEQ ID NO 13
<211> LENGTH: 18
<212> TYPE: DNA
<213> ORGANISM: Artificial sequence
<220> FEATURE:
<223> OTHER INFORMATION: oligonucleotide primer

<400> SEQUENCE: 13
tgggaccctg cccttttt                                                  18

<210> SEQ ID NO 14
<211> LENGTH: 19
<212> TYPE: DNA
<213> ORGANISM: Artificial sequence
<220> FEATURE:
<223> OTHER INFORMATION: oligonucleotide primer

<400> SEQUENCE: 14
ccagcctcag tgagctcca                                                 19

<210> SEQ ID NO 15
<211> LENGTH: 33
<212> TYPE: DNA
<213> ORGANISM: Artificial sequence
<220> FEATURE:
<223> OTHER INFORMATION: oligonucleotide primer

<400> SEQUENCE: 15
tcatattcta atcaagacta gtgactttag agc                                 33

<210> SEQ ID NO 16
<211> LENGTH: 26
<212> TYPE: DNA
<213> ORGANISM: Artificial sequence
<220> FEATURE:

```
<223> OTHER INFORMATION: Oligonucleotide primer

<400> SEQUENCE: 16
aactatggat ccttctcttg tgttgg                                    26

<210> SEQ ID NO 17
<211> LENGTH: 26
<212> TYPE: DNA
<213> ORGANISM: Artificial sequence
<220> FEATURE:
<223> OTHER INFORMATION: oligonucleotide primer

<400> SEQUENCE: 17
ggtaatcagt ggtgtcaaat aggagg                                    26

<210> SEQ ID NO 18
<211> LENGTH: 24
<212> TYPE: DNA
<213> ORGANISM: Artificial sequence
<220> FEATURE:
<223> OTHER INFORMATION: oligonucleotide primer

<400> SEQUENCE: 18
ggtctaagtg atgacagccg tacc                                      24

<210> SEQ ID NO 19
<211> LENGTH: 15
<212> TYPE: DNA
<213> ORGANISM: Artificial sequence
<220> FEATURE:
<223> OTHER INFORMATION: oligonucleotide primer

<400> SEQUENCE: 19
ggcggcggtc acgaa                                                15

<210> SEQ ID NO 20
<211> LENGTH: 19
<212> TYPE: DNA
<213> ORGANISM: Artificial sequence
<220> FEATURE:
<223> OTHER INFORMATION: oligonucleotide primer

<400> SEQUENCE: 20
ttcaggttcc attgccacg                                            19

<210> SEQ ID NO 21
<211> LENGTH: 18
<212> TYPE: DNA
<213> ORGANISM: Artificial sequence
<220> FEATURE:
<223> OTHER INFORMATION: oligonucleotide primer

<400> SEQUENCE: 21
cgtgacgaag agtcagct                                             18

<210> SEQ ID NO 22
<211> LENGTH: 21
<212> TYPE: DNA
<213> ORGANISM: Artificial sequence
<220> FEATURE:
<223> OTHER INFORMATION: oligonucleotide primer

<400> SEQUENCE: 22
cccatcagac tcaccctgaa g                                         21

<210> SEQ ID NO 23
```

```
<211> LENGTH: 22
<212> TYPE: DNA
<213> ORGANISM: Artificial sequence
<220> FEATURE:
<223> OTHER INFORMATION: oligonucleotide primer

<400> SEQUENCE: 23
tgccacaact accaatcctt tt                                              22

<210> SEQ ID NO 24
<211> LENGTH: 28
<212> TYPE: DNA
<213> ORGANISM: Artificial sequence
<220> FEATURE:
<223> OTHER INFORMATION: oligonucleotide probe

<400> SEQUENCE: 24
gctgcagata ccatcatcct ggcttcaa                                        28

<210> SEQ ID NO 25
<211> LENGTH: 28
<212> TYPE: DNA
<213> ORGANISM: Artificial sequence
<220> FEATURE:
<223> OTHER INFORMATION: oligonucleotide probe

<400> SEQUENCE: 25
gacactcttg cagattagtc caggcaga                                        28

<210> SEQ ID NO 26
<211> LENGTH: 25
<212> TYPE: DNA
<213> ORGANISM: Artificial sequence
<220> FEATURE:
<223> OTHER INFORMATION: oligonucleotide probe

<400> SEQUENCE: 26
aagccagtgc cagaagagcc aagga                                           25

<210> SEQ ID NO 27
<211> LENGTH: 22
<212> TYPE: DNA
<213> ORGANISM: Artificial sequence
<220> FEATURE:
<223> OTHER INFORMATION: oligonucleotide probe

<400> SEQUENCE: 27
cgcgatcaca tggtcctgct gg                                              22

<210> SEQ ID NO 28
<211> LENGTH: 24
<212> TYPE: DNA
<213> ORGANISM: Artificial sequence
<220> FEATURE:
<223> OTHER INFORMATION: oligonucleotide probe

<400> SEQUENCE: 28
caccattcac acagcccacg agca                                            24

<210> SEQ ID NO 29
<211> LENGTH: 18
<212> TYPE: DNA
<213> ORGANISM: Artificial sequence
<220> FEATURE:
<223> OTHER INFORMATION: oligonucleotide probe

<400> SEQUENCE: 29
```

```
ttctagtgag cctccgac                                                   18

<210> SEQ ID NO 30
<211> LENGTH: 26
<212> TYPE: DNA
<213> ORGANISM: Artificial sequence
<220> FEATURE:
<223> OTHER INFORMATION: oligonucleotide probe

<400> SEQUENCE: 30
tgtgacaagc tgcatgtgga tcctga                                          26

<210> SEQ ID NO 31
<211> LENGTH: 33
<212> TYPE: DNA
<213> ORGANISM: Artificial sequence
<220> FEATURE:
<223> OTHER INFORMATION: oligonucleotide probe

<400> SEQUENCE: 31
caacttcatt tcacacatga ctttgctgag aaa                                  33

<210> SEQ ID NO 32
<211> LENGTH: 2259
<212> TYPE: DNA
<213> ORGANISM: Artificial sequence
<220> FEATURE:
<223> OTHER INFORMATION: Synthetic construct

<400> SEQUENCE: 32
gatccatagt tcatcattta aaaagaaaaa caaaatagaa aaaggaaaac tatttctgag      60
cataagaagt tgtagggtaa gtctttaaga aggtgacaat ttctgccaat caggatttca    120
aagctcttgc tttgacaatt ttggtctttc agaatactat aaatataacc tatattataa    180
tttcataaag tctgtgcatt ttctttgacc caggatattt gcaaaagaca tattcaaact    240
tccgcagaac actttatttc acatatacat gcctcttata tcagggatgt gaaacagggt    300
cttgaaaact gtctaaatct aaacaatgc taatgcaggt ttaaatttaa taaaataaaa     360
tccaaaatct aacagccaag tcaaatctgt atgtttaac atttaaaata ttttaaagac     420
gtcttttccc aggattcaac atgtgaaatc ttttctcagg gatacacgtg tgcctagatc    480
ctcattgctt tagtttttta cagaggaatg aatataaaaa gaaaatactt aaattttatc    540
cctcttacct ctataatcat acataggcat aattttttaa cctaggctcc agatagccat    600
agaagaacca acactttct gcgtgtgtga gaataatcag agtgagattt ttcacaagt      660 acctgatgag ggttgagaca ggtagaaaaa gtgagagatc tctatttatt tagcaataat    720
agagaaagca tttaagagaa taagcaatg gaaataagaa atttgtaaat ttccttctga    780
taactagaaa tagaggatcc agtttctttt ggttaaccta aattttattt cattttattg    840 ttttattttta ttttatttta ttttatttttg tgtaatcgta gtttcagagt gttagagctg    900
aaaggaagaa gtaggagaaa catgcaaagt aaaagtataa cactttcctt actaaaccga    960
ctgggtttcc aggtaggggc aggattcagg atgactgaca gggccctttag gaacactga   1020 gaccctacgc tgacctcata aatgcttgct accttttgctg ttttaattac atcttttaat   1080
agcaggaagc agaactctgc acttcaaaag ttttttcctca cctgaggagt taatttagta   1140
caaggggaaa aagtacaggg ggatgggaga aaggcgatca cgttgggaag ctatagagaa   1200
agaagagtaa attttagtaa aggaggttta acaaacaaa atataaagag aaataggaac   1260
ttgaatcaag gaaatgattt taaaacgcag tattcttagt ggactagagg aaaaaaataa   1320
```

```
tctgagccaa gtagaagacc ttttcccctc ctaccoctac tttctaagtc acagaggctt    1380
tttgttcccc cagacactct tgcagattag tccaggcaga aacagttaga tgtccccagt    1440
taacctccta tttgacacca ctgattaccc cattgatagt cacactttgg gttgtaagtg    1500
actttttatt tatttgtatt tttgactgca ttaagaggtc tctagttttt tatctcttgt    1560
ttcccaaaac ctaataagta actaatgcac agagcacatt gatttgtatt tattctattt    1620
ttagacataa tttattagca tgcatgagca aattaagaaa acaacaaca aatgaatgca     1680 tatatatgta tatgtatgtg tgtatatata cacatatata tatatttt ttttctttc      1740 ttaccagaag gttttaatcc aaataaggag aagatatgct tagaactgag gtagagtttt   1800
catccattct gtcctgtaag tattttgcat attctggaga cgcaggaaga gatccatcta   1860
catatcccaa agctgaatta tggtagacaa agctcttcca cttttagtgc atcaatttct    1920
tatttgtgta ataagaaaat tgggaaaacg atcttcaata tgcttaccaa gctgtgattc    1980
caaatattac gtaaatacac ttgcaaagga ggatgttttt agtagcaatt tgtactgatg    2040
gtatggggcc aagagatata tcttagaggg agggctgagg gtttgaagtc caactcctaa    2100
gccagtgcca gaagagccaa ggacaggtac ggctgtcatc acttagacct caccctgtgg    2160
agccacaccc tagggttggc caatctactc ccgagccatc tattgcttac atttgcttct    2220
gacacaactg tgttcactag caacctcaaa cagacacca                           2259

<210> SEQ ID NO 33
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 33
ggacagcaag aaagcgagct                                                  20

<210> SEQ ID NO 34
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 34
tgagtaatag tttcctgatt ctccca                                           26

<210> SEQ ID NO 35
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 35
tcagaaagtg gtggctggtg                                                  20

<210> SEQ ID NO 36
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 36
aaagtcactc tcatggaaac agaca                                            25
```

```
<210> SEQ ID NO 37
<211> LENGTH: 28
<212> TYPE: DNA
<213> ORGANISM: Artificial sequence
<220> FEATURE:
<223> OTHER INFORMATION: Oligonucleotide probe

<400> SEQUENCE: 37
gctaatgccc tggcccacaa gtatcact                                            28

<210> SEQ ID NO 38
<211> LENGTH: 25
<212> TYPE: DNA
<213> ORGANISM: Artificial sequence
<220> FEATURE:
<223> OTHER INFORMATION: Oligonucleotide probe

<400> SEQUENCE: 38
ccccaacccc tggaaaccat acctc                                               25
```

USE OF REPLICATORS TO PREVENT GENE SILENCING

REFERENCE TO RELATED APPLICATIONS

This is the U.S. National Stage of International Application No. PCT/US2006/034812, filed Sep. 7, 2006, which was published in English under PCT Article 21(2), which in turn claims the benefit of U.S. Provisional Application No. 60/715,113, filed Sep. 7, 2005. Both applications are incorporated herein in their entirety.

FIELD OF THE DISCLOSURE

This disclosure relates to the field of regulatory elements, specifically to replicators and transgene constructs containing replicator nucleic acid sequences. It also relates to the use of such replicators and transgene constructs to inhibit, delay, or prevent gene silencing.

BACKGROUND

Gene transfer (also known as gene therapy) is a relatively new technology for the treatment of rare genetic disorders and common multifactorial diseases. Eukaryotes are equipped to protect the genome and oppose the expression of abnormal or foreign transcription units. As a result, a transgene construct introduced into a cell can trigger transcriptional silencing wherein, after a period of expression, expression of the coding sequence in the transgene construct declines to undetectable levels without the loss of the construct.

The expression of therapeutic coding sequences can be augmented by including genetic control elements, such as promoters, that control expression of the gene in response to systemically administered drugs. In other strategies, vectors are engineered to include cis-modifications of retroviral vector sequences, for example mutations of virus silencer elements, in order to prevent silencing of the transgene (Ellis et al., *Curr Gene Ther.*, 5:367-73, 2005). Vectors can also be designed to include strong positive regulatory elements and insulators, and to avoid the use of non-mammalian reporter genes. However, gene silencing (the conversion of an actively expressed gene, or coding sequence, to a non-expressed gene that occurs without a change in the primary DNA sequence) continues to be a major impediment in gene therapy and a need exists for developing methods of inhibiting gene silencing.

SUMMARY

Disclosed herein are transgene constructs, comprising a coding nucleic acid sequence to be expressed in a cell and a metazoan replicator nucleic acid sequence. In specific contemplated embodiments, the metazoan replicator nucleic acid sequence integrates into a host genome, thereby integrating the transgene into the genome. The replicator nucleic acid sequence alters the timing of DNA replication of the transgene construct, e.g., from late S phase to early S phase, thereby inhibiting silencing of the coding nucleic acid sequence. Also provided herein are methods of inhibiting or delaying gene silencing in a cell.

Prior to this disclosure, replicators were known to those of skill in the art to be genetic elements required for the initiation of DNA replication from a particular chromosomal location and were defined genetically based on their ability to confer initiation of DNA replication in cis at ectopic sites. As disclosed herein, replicators not only affect the location of initiation events, but also influence chromatin structure and modulate the timing of DNA replication.

The foregoing and other features and advantages will become more apparent from the following detailed description of several embodiments, which proceeds with reference to the accompanying figures.

BRIEF DESCRIPTION OF THE FIGURES

FIG. 1 provides a mammalian experimental system in which replication timing could be altered in a controlled manner.

FIG. 2 illustrates that changes of replication timing in the transgene precede transcriptional silencing of gene expression and chromatin condensation. FIG. 2A is a digital image showing GFP expression of MEL cells harboring the miniLCR-pro-GFP-HS4 cassette (construct II, FIG. 1C) in the silent orientation at RL4, 3 and 8 weeks after transfection. FIG. 2B is a graph representing the replication timing of cells inserted with the miniLCR-pro-GFP-HS4 cassette in the silencing-prone orientation 3 weeks after transfection. Specific transgene and host sequences in newly replicated DNA were detected by real-time polymerase chain reaction (PCR).

FIG. 3 illustrates the effect of a DNA replicator on replication timing.

FIG. 5 illustrates effects of a replicator on transgene expression. Transgenes were transfected using RMCE into the RL4 site with/without a replicator. Expression of the GFP marker was monitored by Fluorescence Activated Cell Sorting (FACS) at the indicated time after transfection.

FIG. 6 illustrates that replicators can prevent chromatin deacetylation and gene silence at an unlinked site on chromosome 4 (RL5).

SEQUENCE LISTING

Figures 1A, 1B, 1C:
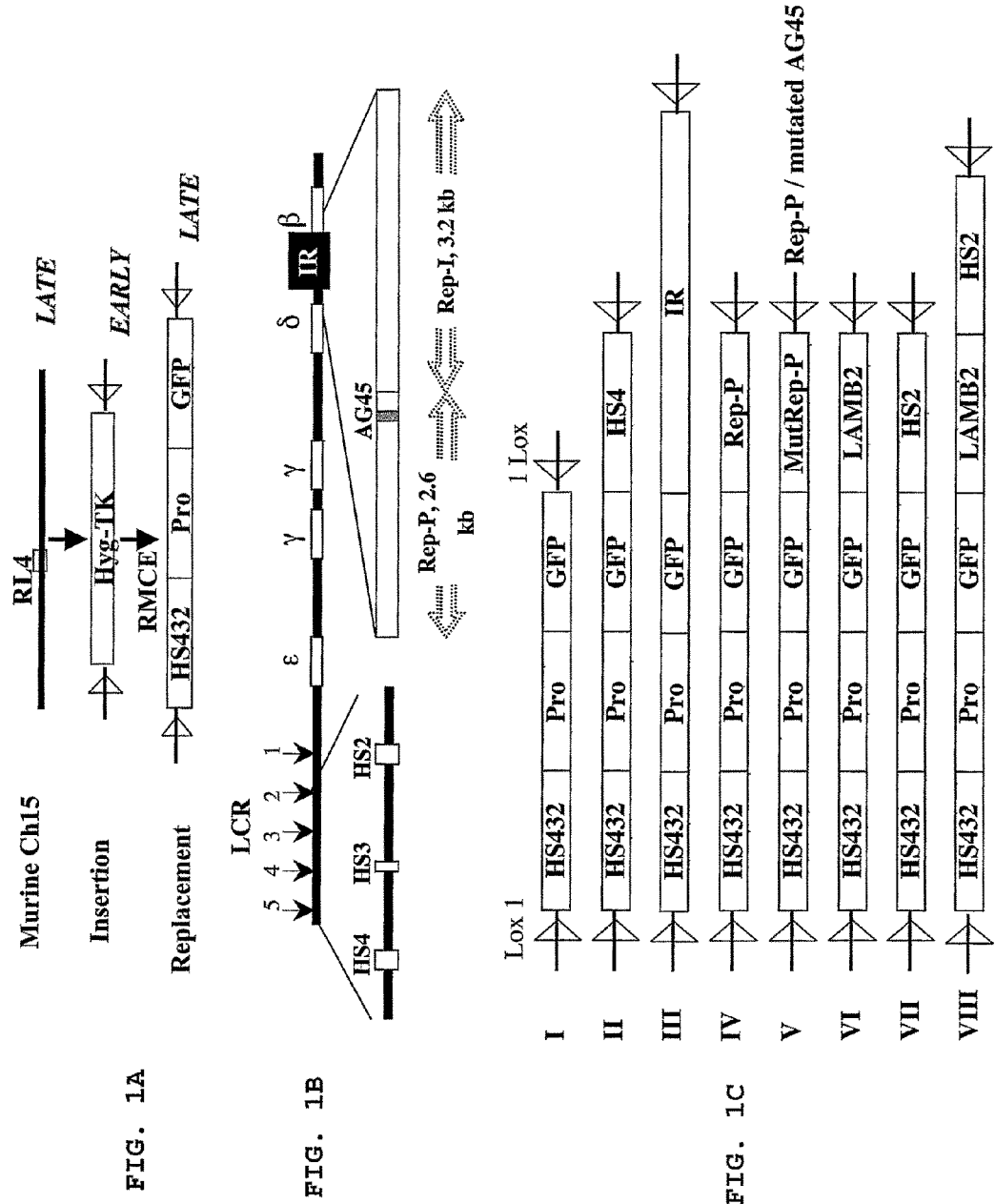
FIG. 1A is a schematic representation of the experimental system used (Lin et al., *Curr Biol* 13:1019, 2003). The Cre recombinase-mediated cassette exchange (RMCE) technique was used for precise replacement of sequences inserted within a late-replicating site in murine chromosome 15 (RL4). A cassette encoding for antibiotic resistance markers was first inserted in this locus, then replaced by sequences from the human β-globin locus. Hyg: hygromycin, TK: thymidine kinase, GFP: green fluorescent protein.
FIG. 1B is a schematic representation of the human β-globin locus. Sequences used include the locus control region (LCR) core region (DNAse hypersensitive sites 4, 3, and 2: HS432); the β-globin promoter (Pro); IR, the β-globin replication initiation region; Rep-P, one of the two replicators within IR; mutated Rep-P with 45-bp AG-rich sequence (AG45) replacement (Mut RepP) (Wang et al., *Mol Cell Biol* 24:3373, 2004); and human lamin B2 (LAMB2) replicator (positions 3691 to 4978, GenBank Accession No. M94363).
FIG. 1C is a schematic representation of the constructs used. These constructs were transfected into MEL cells either at the RL4 site (chromosome 15) or at the RL5 site (chromosome 4) (Feng et al., *Mol. Cell. Biol.* 21:298-309, 2001).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Public database Accession numbers provided herein are understood to apply to the release of the referenced sequence available as of the day this application is filed. In the accompanying sequence listing:

SEQ ID NO: 1 is the nucleic acid sequence of the human β-globin locus initiation region and corresponds to positions 59882 to 64557 of GenBank Accession Number U01317.1.

SEQ ID NO: 2 is the nucleic acid sequence of the human β-globin locus replicator Rep-I and corresponds to positions 62187 to 64557 of GenBank Accession Number U01317.1 (which corresponds to positions 2307 to 4680 of SEQ ID NO: 1).

SEQ ID NO: 3 is the nucleic acid sequence of the human β-globin locus replicator Rep-P and corresponds to positions 59882 to 62187 of GenBank Accession Number U01317.1 (which corresponds to positions 1 to 2307 of SEQ ID NO: 1).

SEQ ID NO: 4 is the nucleic acid sequence of the human Lamin B2 replicator and corresponds to positions 3691 to 4978 in GenBank Accession Number M94363.

SEQ ID NO: 5 is the nucleic acid sequence including the human c-myc origin and replicator sequence, which encompasses approximately residues 0-2400 of the c-myc gene, GenBank Accession Number X00364 (Malott, M., and Leffak, M. (1999) *Mol. Cell. Biol.* 19, 5685-5695).

SEQ ID NO: 6 is the nucleic acid sequence of the Chinese hamster dihydrofolate reductase (DHFR) initiation region, which encompasses residues 1-5800 of GenBank Accession Number Y09885 (Altman and Fanning, *Mol Cell Biol.* 24 (10):4138-50, 2004).

SEQ ID NO: 7 is the nucleic acid sequence of the *Drosophila melanogaster* chorion gene initiation region, which comprises nucleotides 1-3850 of GenBank Accession Number CG4049 (Levine and Spradling, *Chromosoma*, 92 (2), 136-142, 1985).

SEQ ID NOS: 8-15, 33 and 34 are forward primers.
SEQ ID NOS: 16-23, 35, and 36 are reverse primers.
SEQ ID NOS: 24-31, 37, and 38 are probes.
SEQ ID NO: 32 is the nucleic acid sequence of the dysfunctional variant of Rep-P (Rep-P including a deletion of the AG-rich region at positions 62074 to 62118 of GenBank Accession Number U01317.1, which corresponds to positions 2193 to 2237 of SEQ ID NO: 1).

DETAILED DESCRIPTION

I. General Overview

Disclosed herein are transgene constructs and methods of inhibiting gene silencing in a cell. Prior to this disclosure, replicators were known to those of skill in the art to be genetic elements required for the initiation of DNA replication from a particular chromosomal location and were defined genetically based on their ability to confer initiation of DNA replication in cis at ectopic sites. As disclosed herein, replicators not only affect the location of initiation events, but also influence chromatin structure and modulate the timing of DNA replication.

Provided herein is a transgene construct that includes a coding nucleic acid sequence to be expressed in the cell and a metazoan replicator nucleic acid sequence, wherein the metazoan replicator nucleic acid sequence integrates into a host genome. The metazoan replicator nucleic acid sequence alters timing of DNA replication of the transgene from late S phase to early S phase and inhibits silencing of the coding nucleic acid sequence.

In one embodiment of the transgene construct, the coding nucleic acid sequence encodes a therapeutic product. In another embodiment, the transgene construct includes an adenoviral or a retroviral sequence. In yet another embodiment of the transgene construct, the metazoan replicator is a human β-globin locus, human LaminB locus, human c-myc locus, Chinese hamster dihydrofolate reductase, or a *Drosophila* chorion gene replicator.

A method of inhibiting silencing of a gene in a cell is also provided herein. The method includes introducing into the cell a transgene construct that includes a coding nucleic acid sequence to be expressed in the cell and a metazoan replicator nucleic acid sequence. The metazoan replicator nucleic acid sequence alters timing of DNA replication of the transgene from late S phase to early S phase and inhibits silencing of the coding nucleic acid sequence.

In one embodiment of the method, the cell is a mammalian cell, or in more specific examples, a human cell. In other embodiments of the method, the transgene construct is introduced into the cell by homologous recombination, recombinase-mediated cassette exchange, or microinjection.

Also provided herein is an improved method of expressing a coding nucleic acid sequence in a cell, wherein a transgene construct comprising the coding nucleic acid sequence is introduced into a cell. The improvement includes introducing into the cell a metazoan replicator nucleic acid sequence, which alters timing of DNA replication of the coding nucleic acid sequence from late S phase to early S phase, thereby inhibiting silencing of the coding nucleic acid sequence.

In one embodiment of the method, the coding nucleic acid sequence encodes a therapeutic product. In another embodiment of the method, the cell is a mammalian cell, or in more specific examples, a human cell. In other embodiments, the transgene construct includes an adenoviral or a retroviral sequence. Also provided is a method in which the transgene construct is introduced into the cell by homologous recombination, recombinase-mediated cassette exchange, or microinjection. Further provided are methods in which the metazoan replicator is a human β-globin locus, human LaminB locus, human c-myc locus, Chinese hamster dihydrofolate reductase, or a *Drosophila* chorion gene replicator.

II. Abbreviation

| | |
|---|---|
| ACE3 | amplification control region 3 |
| ADA | adenosine deaminase |
| ADAMTS13 | a disintegrin and metalloproteinase with thrombospondin repeats |
| AERd | amplification enhancer region d |
| DHFR | dihydrofolate reductase |
| FACS | fluorescence activated cell sorter |
| GFP | green fluorescence protein |
| gpt | guanine phosphoribosyl transferase |
| hisD | histidinol dehydrogenase |
| Hyg | hygromycin |
| IR | initiation region |
| LAMB2 | laminin B2 |
| LCR | locus control region |
| mAmy | murine amylase |
| mAmylase | murine amylase |
| MDR1 | multidrug resistance-1 |
| MutRep-P | mutated Rep-P |
| OBR | origin of bidirectional DNA replication |
| OPR | the origin-protected region |
| PCR | polymerase chain reaction |
| Pro | human β-globin promoter |
| RMCE | recombinase-mediated cassette exchange |
| TK | thymidine kinase |

III. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

Cell cycle: An ordered set of events, culminating in cell growth and division into two daughter cells. Non-dividing cells are not considered to be in the cell cycle. The phases of the cell cycle are G1-S-G2-M. The G1 phase represents "GAP 1." The S phase represents "Synthesis." This is the stage when DNA replication occurs. Expressed genes replicate early (first half of S phase) whereas silent genes replicate later. The G2 phase represents "GAP 2." The M phase represents "mitosis", and is when nuclear (chromosomes separate) and cytoplasmic (cytokinesis) division occur.

Coding nucleic acid sequence: A nucleic acid sequence that encodes a functional molecule. The nucleic acid can encode a protein, such as a therapeutic polypeptide, or a functional nucleic acid sequence, such as an antisense sequence. When transferred to a host cell, such as in gene therapy, a coding nucleic acid sequence can alter the function of the host cell.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

DNA replication: The use of existing DNA as a template for the synthesis of new DNA strands. In humans and other eukaryotes, replication occurs in the cell nucleus. In mammalian chromosomes, DNA replication begins at multiple initiation regions with an average spacing of 50-150 kb apart, these define replicons. Replication begins at some replication origins earlier in S phase than at others, but the process is completed by the end of S phase.

DNAse hypersensitive (HS) sites: Sequences in genomic DNA that are characterized by hypersensitivity to DNAse I digestion (are accessible to digestion by very low levels of DNAse I) in isolated nuclei. These sites tend to be, but are not always, at or near active genes, which are transcribed or which may be regularly transcribed. DNA segments which contain active genes tend to be more sensitive to being digested by DNAse I than inactivate genes, because the inactivate genes are generally within condensed regions of the chromosome, tightly associated with histones, while the active genes are in regions of DNA that is in more open configurations for easy access for transcription.

Also recognized are DNAse sensitive regions or sites—portions of the genome or specific sites that are digested more readily than insensitive regions, but are not the most hypersensitive. It is not clear at this point exactly what sensitive sites are, nor how they differ from hypersensitive sites. It is contemplated herein that at least some embodiments of the provided methods isolate a mixture of both hypersensitive and sensitive sites. Thus, when the term "hypersensitive site" is used, it is understood that the digestion sites can include DNAse hypersensitive sites, DNAse sensitive sites, and mixtures of both.

More particularly, DNAse HS sites are correlated with nucleosome-free (or relatively nucleosome free) regions of the genome. This has been exploited to identify regulatory elements in genomic DNA, using a technique referred to as DNAse HS site mapping. This method uses limited digestion of genomic DNA with DNAse, followed by complete digestion with a restriction endonuclease (such as EcoRI) and Southern blotting of the digested material, to study and identify the location of regulatory elements. DNAse HS sites have been associated with a number of gene regulatory elements, including promoters, enhancers, suppressors, insulators, transcriptional terminators, origins of replication, and locus control regions.

Gene therapy (also referred to as Gene transfer): Introduction of a heterologous nucleic acid molecule (transgene) into one or more recipient cells, wherein expression of the heterologous nucleic acid in the recipient cell affects the cell's function and results in a therapeutic effect in a subject. For example, the heterologous nucleic acid molecule may encode a protein that affects a function of the recipient cell. In another example, the heterologous nucleic acid molecule may encode an anti-sense or small inhibitory RNA (siRNA) nucleic acid that is complementary to a nucleic acid molecule present in the recipient cell, and thereby affect a function of the corresponding native nucleic acid molecule. In still other examples, the heterologous nucleic acid may encode a ribozyme or deoxyribozyme, which are capable of cleaving nucleic acid molecules present in the recipient cell. The heterologous nucleic acid may be integrated into the genome of a cell, for instance a somatic cell or a germ cell of an organism such as a multicellular organism or more particularly a subject.

Two types of gene therapy have been identified: (1) somatic cell therapy, in which cells other than germ cells are genetically altered, and (2) germ line therapy, in which a replacement gene is integrated into the genome of a subject's gametes or their precursors, resulting in expression of the new gene in the subject's offspring and subsequent generations. The fundamental difference between germ line gene therapy and somatic cell gene therapy is that germ line gene therapy affects the welfare of subsequent generations and may be associated with increased risk and the potential for unpredictable and irreversible results.

Gene therapy can be broadly split in to two categories: ex vivo and in vivo. Recombination-based approaches in vivo are especially uncommon, because for most DNA constructs recombination is a very low probability event. In the ex vivo approach cells are removed from the subject's body and incubated with vectors that inserted copies of the genes. Most gene-therapy vectors are viruses, which have evolved a mechanism to encapsulate and deliver their genes to human cells in a pathogenic manner. However, viruses cause problems such as toxicity, immune and inflammatory responses, and gene control and targeting issues. Alternatives to using viruses to deliver genes into cells are being explored, such as directly introducing DNA into cells by microinjection and the development of human artificial chromosomes (HACs) that, when introduced into human cells, would exist autonomously along side the standard 46 chromosomes.

After modification, the cells are transplanted back in to the patient where they replicate and produce functional descendants for the life of the transplanted individual. In the in vivo approach, the vectors must deliver the genes to enough cells for results to be achieved and they have to remain undetected by the body's immune system. There are two classes of viruses which have been used as in vivo vectors—retroviruses and adenoviruses.

Genomic DNA: The DNA found within the nucleus and containing an organism's genome, which is passed on to its offspring as information for continued replication and/or propagation and/or survival of the organism. The term can be used to distinguish between other types of DNA, such as DNA found within plasmids or organelles.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

The following is an exemplary set of hybridization conditions and is not limiting:
Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 50% identity)
Hybridization: 6×SSC at RT to 55° C. for 16-20 hours
Wash at least twice: 2×-3×SSC at RT to 55° C. for 20-30 minutes each.

Initiator: Proteins or protein complexes that bind replicators and are required for initiation of DNA replication.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of nucleotides joined by native phosphodiester bonds, between about 4 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or intersugar linkages, such as a phosphorothioate oligodeoxynucleotide. Functional analogs of naturally occurring polynucleotides can bind to RNA or DNA, and include PNA molecules.

Particular oligonucleotides and oligonucleotide analogs include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Specifically contemplated herein are oligonucleotides that contain one or more modified nucleotides, for instance modified by phosphorylation or the presence of a labeling or other identification molecule (such as, for instance, biotin or another binding agent). By way of example, phosphorylation at the end of oligonucleotides (or pairs of oligonucleotides, hybridized to one another) can facilitate ligation of the oligonucleotide to a blunted end of a nucleic acid molecule.

Operably Linked: A first nucleic acid sequence is operably linked with a second nucleic acid sequence when the first nucleic acid sequence is placed in a functional relationship, or in cis, with the second nucleic acid sequence. Operably linked sequences are in proximity to each other. For instance, a replicator is operably linked to a coding sequence if the replicator affects the transcription or expression of the coding sequence or transgene. A replicator can be operably linked to more than one element and/or nucleic acid sequence, such as a promoter and a coding sequence (or transgene). By way of example, these elements might be right next to (adjacent to) each other. Alternatively, an enhancer element, such as a replicator or a promoter, and a coding sequence might be large distances away from each other, for instance even greater than 250 kb apart. Other optimal distances include 0.5, 1, 5, 10, 20, 50, 100, 200 kb. Generally, operably linked DNA sequences are contiguous and, where necessary to join two protein-coding regions, in the same reading frame.

Probes and Primers: Nucleic acid probes and primers can be readily prepared based on the nucleic acid molecules provided herein, or isolated from libraries generated using the provided methods. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g. in Sambrook et al. (*In Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand. Optionally, the primer then can be extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence, for example, by using computer programs intended for that purpose such as Primer (Version 0.5,© 1991, Whitehead Institute for Biomedical Research, Cambridge, Mass.).

One of ordinary skill in the art will appreciate that the specificity of a particular probe or primer increases with its length. Thus, for example, a molecule comprising 30 consecutive nucleotides of a target protein encoding nucleotide will anneal to a target sequence, such as another homolog of the original target protein, with a higher specificity than a corresponding primer of only 15 nucleotides. Thus, in order to obtain greater binding specificity, probes and primers can be selected that comprise at least 20, 23, 25, 30, 35, 40, 45, 50 or more consecutive nucleotides of a protein-encoding nucleotide sequences. These molecules may be obtained from any region of a sequence (for example, a target nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, for example about eighths, sixteenths, twentieths, fiftieths, and so forth, with similar effect. Another mode of division is to select the 5' (upstream) and/or 3' (downstream) region of a gene.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In particular embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters include, but are not limited to the β-globin promoter, SV40 promoter, the CMV enhancer-promoter, the CMV enhancer/β-actin promoter, and the tissue-specific promoters, such as probasin, and promoters that respond to specific transcription factors that are altered in malignancies, such as myc and TP53.

Other promoter sequences which can be used to construct the transgene nucleic acids and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In one embodiment, a promoter is a strong promoter, which promotes transcription of RNA at high levels, for example at levels such that the transcriptional activity of the promoter generally accounts for about 25% of transcriptional activity of all transcription within a cell. The strength of a promoter is often tissue-specific and thus may vary from one cell type to another. For example, CMV is a classic strong promoter because it generates high levels of transcriptional activity in many cell types. Examples of strong promoters include, but are not limited to: CMV; CMV/chicken β-actin; elongation factors 1A and 2A; SV40; RSV; and the MoLV LTR.

In another embodiment, a promoter is a tissue-specific promoter, which promotes transcription in a single cell type or narrow range of tissues. Examples of tissue-specific promoters include, but are not limited to: probasin (which promotes expression in prostate cells), an immunoglobulin promoter; a whey acidic protein promoter; a casein promoter; glial fibrillary acidic protein promoter; albumin promoter; β-globin promoter; and the MMTV promoter.

In yet another embodiment, a promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

Protein: A biological molecule expressed by a gene or recombinant or synthetic coding sequence and comprised of amino acids, with or without one or more modifications.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Regulatory Sequences or Elements: These terms refer generally to a class of DNA sequences that influence or control expression of genes. Included in the term are promoters, enhancers, locus control regions, boundary elements/insulators, silencers, Matrix attachment regions (also referred to as scaffold attachment regions), repressor, replicators, transcriptional terminators, replication origin, and meiotic recombination hotspots. Promoters are sequences of DNA near the 5' end of a gene that act as a binding site for RNA polymerase, and from which transcription is initiated (see above). Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also know as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Replicators are genetic elements required for initiation of DNA replication from a particular chromosomal location (see below). Transcriptional terminators are regions within the gene vicinity that RNA Polymerase is released from the template. Replication origins (also referred to as initiation regions) are regions of the genome, during DNA synthesis or replication phases of cell division, from which replication forks emanate and from where the replication process of DNA begins. Meiotic recombination hotspots are regions of the genome that recombine more frequently than the average during meiosis.

Replicator: A regulatory sequence or genetic element required for the initiation of DNA replication from a particular chromosomal location.

A replicator is encoded by a replicator nucleic acid sequence.

Replicators are defined genetically, based on their ability to confer initiation of DNA replication in cis at ectopic sites. In single-cell eukaryotes, such as *Saccharomyces cerevisiae*, replication is initiated from relatively simple replicators that may also function as Autonomously Replicating Sequences (ARS) in plasmids outside their natural chromosomal context. Metazoan replicators lack a common consensus sequence and require chromosomal context to initiate replication. Metazoan replicators are identified by their ability to confer initiation of DNA replication when transferred from their native locations to ectopic locations on other chromosomes.

The length of DNA typically shown to have ectopic replicator activity ranges from 1.2 kb to 5.8 kb. Mutational analysis of various replicators has identified that metazoan replicators are composed of several non-redundant sequence-specific modules that cooperate to direct local initiation of replication. For example, the *Drosophila melanogaster* chorion gene locus (2.3 kb) requires two distinct sequences (Ori-β (840 bp) and ACE3 (Amplification Control element of chromosome 3; 320 bp); Lu et al., *Genes Dev.*, 15:134-146, 2001; Zhang and Tower, *Development*, 131:2089-2099, 2004); the Chinese hamster DHFR replicator (5.8 kb) requires at least four elements for the initiation of DNA replication at ectopic loci (Altman and Fanning, *Mol. Cell Biol.*, 21: 1098-1110, 2001); the lamin B2 replicator (LMNB2; 1.2 kb) requires a 290 bp region and is enhanced by a separate element (Paixao et al., *Mol. Cell Biol.*, 24:2958-2967, 2004); the human c-myc replicator (2.4 kb)) requires several elements (Liu et al., *Mol. Cell Biol.*, 23:1832-1842, 2003); and the human β-globin replicator contains two-non-overlapping independent replicators (Rep-P (2.6 kb) and Rep-I (3.2 kb)) and initiation within each of these requires at least two distinct sequence elements (Wang et al., *Mol. Cell Biol.*, 24: 3373-3386, 2004).

AT-rich sequences (symmetric and asymmetric) have been identified in the DHFR ori-β, c-myc and β-globin replicators, and are important for ectopic replicator activity in these systems, as well as at the *Drosophila* chorion gene locus (Altman and Fanning, *Mol. Cell Biol.*, 21: 1098-1110, 2001). Other AT-rich sequences that are important for ectopic ori-β replicator activity include an intrinsically bent DNA that is dictated by five $A_{3-4}$ stretches spaced at ten-nucleotide intervals, binding sites for the conserved polydactyl zinc-finger protein RIP60 formed by $(TTA)_{4-5}$ (Altman and Fanning, *Mol. Cell Biol.*, 24: 4138-4150, 2004), and a 109 bp region that cooperates with the other modules to dictate initiation. Other DNA sequences, which are not AT-rich, can cooperate with AT-rich stretches to form efficient replicators (Aladjem and Fanning, *EMBO reports*, 5:686-691, 2004).

Replicon: A unit of DNA whose replication is controlled through a replicator. Each metazoan chromosome contains many tandemly organized replicons, activated to replicate at different moments in S-phase by interaction with specific replication initiators.

Sequence Identity: The similarity between two nucleic acid sequences, or two amino acid sequences, is expressed in terms of sequence identity. Sequence identity is frequently measured in terms of percentage identity (or similarity or homology); the higher the percentage, the more similar the two sequences are. Homologs or orthologs of a gene sequence(s), will possess a relatively high degree of sequence identity when aligned using standard methods. This homology will be more significant when the orthologous nucleic acid sequences or genes are derived from species that are more closely related (for example, human and chimpanzee sequences), compared to species more distantly related (for example, human and *C. elegans* sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene*, 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. When aligning short sequences (fewer than around 30 nucleic acids), the alignment can be performed using the BLAST short sequences function, set to default parameters (expect 1000, word size 7).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (*In Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a protein-encoding sequence will typically hybridize to a probe based on either an entire protein-encoding or a non-protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

It is recognized that DNA can encode non-protein functional elements. Thus, nucleic acid sequences that do not show a high degree of sequence identity may nevertheless encode similar elements. It is understood that changes in nucleic acid sequence can produce multiple nucleic acid molecules having substantially the same function.

Silencing: Conversion of an actively expressed gene, or construct, to a non-expressed gene, or construct, which occurs without a change in the primary DNA sequence. Transcriptional silencing refers to the inhibition of transcription of a gene, for example a coding nucleic acid sequence. Post-transcriptional silencing refers to silencing at the RNA level and which results in the inhibition of translation, for example by small inhibitory RNAs (siRNAs).

Subject: Living multi-cellular vertebrate organisms, particularly a mammal, including human and veterinary subjects, such as cows, pigs, horses, dogs, cats, birds, reptiles, mice, rats, and fish.

Transduced and Transfected: A virus or vector transduces or transfects a cell when it transfers nucleic acid into the cell. A cell is "transfected" by a nucleic acid transduced into the cell when the DNA becomes stably replicated by the cell, either by incorporation (integration) of the nucleic acid into the cellular genome, or by episomal replication.

Transgene Construct: A nucleic acid sequence from one organism inserted into the genome of another. The transgene construct can be integrated into the genome of a somatic cell or of a germ cell of an organism (which is thereby rendered transgenic). A transgene construct is generally coding nucleic acid sequence, but can also include regulatory elements, such as promoter, enhancer, or replicator nucleic acid sequences.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Methods of Inhibiting Gene Silencing

Eukaryotes are equipped to protect the genome and oppose the expression of abnormal or foreign transcription units. As a result, a transgene construct introduced into a cell can trigger transcriptional silencing wherein, after a period of expression, levels of the transgene product decline to undetectable levels without the loss of the transgene construct. Thus, gene silencing (the conversion of an actively expressed gene to a non-expressed gene that occurs without a change in the primary DNA sequence) is a major impediment in gene therapy and a need exists for developing methods of inhibiting gene silencing.

Disclosed herein are methods of preventing, delaying, or inhibiting gene silencing in a cell. Prior to this disclosure, replicators were known to those of skill in the art to be genetic elements required for the initiation of DNA replication from a particular chromosomal location and were defined genetically based on their ability to confer initiation of DNA replication in cis at ectopic sites. As disclosed herein, replicators not only affect the location of initiation events, but also influence chromatin structure, modulate the timing of DNA replication, and influence expression (transcription) of transgene sequences.

DNA encoding an actively expressed coding nucleic acid sequence will typically replicate in early S phase, and maintain a decondensed chromatin conformation. In addition, the chromatin at that locus will contain acetylated and methylated histones. In contrast, DNA encoding a silenced coding nucleic acid sequence will typically replicate late in S phase, exhibit a condensed chromatin conformation, and the chromatin at the locus will not be enriched in acetylated and methylated histones.

As disclosed herein, a replicator nucleic acid sequence, when operably linked to another nucleic acid sequence, such as a coding nucleic acid sequence, is capable of preventing, delaying, or inhibiting the silencing of the nucleic acid sequence (transgene construct). Thus, a replicator sequence, which is known to those of skill in the art to regulate DNA replication, is now shown to also regulate transcription of an operably linked nucleic acid sequence.

It is shown here that preventing, delaying, or inhibiting the silencing of a transgene construct is associated with a change in the timing of DNA replication from late S phase to early S phase, decondensation of the chromatin, or methylation and/or acetylation of histones. Thus, preventing, reducing, or delaying the silencing of the transgene construct is associated with one or more of the following: maintaining DNA replication in early S phase, maintaining the chromatin in a decondensed conformation, or maintaining histones methylated and/or acetylated.

The disclosed method includes introducing into a cell of interest a transgene construct which includes a replicator nucleic acid sequence operably linked with (in the proximity of) a coding nucleic acid sequence to be expressed in the cell. Such a construct, when incorporated (integrated) into the genome of a cell, will exhibit one or more of the following characteristics indicative of expression of the transgene: replication in early S phase (early replication), a decondensed chromatin conformation, chromatin with acetylated histones, or chromatin with methylated histones. In one embodiment, a replicator nucleic acid sequence operably linked with (in proximity to) a coding sequence will delay or prevent silencing of the transgene construct.

In another embodiment, a replicator nucleic acid sequence is introduced in the proximity of a silenced coding sequence (e.g., integrated into proximal or adjacent sequence), thereby inhibiting or reversing silencing and allowing for expression of the coding sequence. Inhibition of silencing is associated with a change in timing of replication of the transgene construct from late S phase to early S phase, decondensation of chromatin, acetylation of histones, or methylation of histones, or any combination thereof, thereby inhibiting the silencing of the transgene construct.

Silencing of a coding sequence, gene, or transgene construct, can be inhibited, delayed, or prevented by the disclosed methods and compositions. Thus, disclosed methods and compositions extend the length of time that a gene or transgene construct is expressed. For example, the disclosed methods and compositions can delay or inhibit the initiation of silencing of a gene or transgene construct. In other embodiments, the level of expression of the gene or transgene construct is increased when using the disclosed methods and compositions, compared to methods and compositions lacking a replicator nucleic acid sequence. Under any of the above conditions, the level of expression of the gene or transgene construct in the proximity of a replicator sequence is increased, compared to expression levels in the absence of a replicator sequence.

In one particular embodiment, the introduction (integration) of a replicator sequence in the proximity of a silenced gene or transgene construct inhibits silencing 100% and expression of the gene or transgene construct is increased by 100%. In other embodiments, the introduction of a replicator sequence in the proximity of a silenced gene or transgene construct inhibits silencing at least 99%, at least 95%, at least 90%, at least 85%, at least 80%, at least 75%, such that expression of the gene, or transgene construct, is increased by at least 99%, at least 95%, at least 90%, at least 85%, at least 80%, at least 75%, respectively. In other embodiments, the introduction (integration) of a transgene construct containing a replicator sequence and a coding nucleic acid sequence prevents or delays silencing of the transgene construct by 100%. In further embodiments, the introduction of a transgene construct containing a replicator sequence and a coding nucleic acid sequence prevents or delays silencing of the transgene construct by at least 99%, at least 95%, at least 90%, at least 85%, at least 80%, at least 75%.

Examples of the disclosed method use replicator sequences that include all or any portion of any replicator nucleic acid sequence known to those of ordinary skill in the art, including replicator nucleic acid sequences now or hereafter characterized in any species, for example, human, mouse, or hamster. Metazoan replicator sequences have been shown to be associated with the initiation region (IR) of the human β-globin locus, the human c-myc promoter, the human lamin B2 locus, the Chinese hamster DHFR locus, and the *Drosophila melanogaster* chorion locus. Examples of additional known replication origins are listed in Table 1, below.

TABLE 1

Replication Origins Mapped in Metazoan Genomes

| Origin | Species | Location and Properties | Refs.* |
|---|---|---|---|
| Early ADA origin | Mouse | 28.5 kb upstream of adenosine deaminase gene; | 5 |
| Late ADA origin | Mouse | Intergenic region ~150 kb upstream of ADA gene | 31 |
| APRT origin | Hamster | 5'-end of adenine phosphoribosyl transferase gene; CpG island | 9 |
| ALDOB origin | Rat | Within aldolase B gene promoter region | 22 |
| CAD origin | Hamster | OBR within coding region of the CAD (carbamoyl-phosphate synthetase, aspartate carbamoyltransferase, and dihydroorotase) gene | 18 |
| DHFR origin | Hamster | Intergenic region downstream of dihydrofolate reductase gene; initiation zone containing several preferred initiation sites | 1, 4, 11, 15 |
| DMMT1 origin | Human | Within the introns of the DNA-methyltransferase gene | 2 |
| IGFII origin | Human | Upstream of insulin Growth Factor II gene; CpG island | 9 |
| HBB origin | Chicken | Upstream of β-globin gene; four initiation sites | 27 |
| HBB origin | Human | In the promoter and within the intron of the human β-globin major adult gene | 19, 33 |
| GADD45A | Hamster | Within intron of growth arrest and DNA-damage- | 9 |
| Early ADA origin origin | Mouse | 28.5 kb upstream of adenosine deaminase gene; inducible gene; CpG island | 5 |
| HPRT origin | Human | Upstream of hypoxanthine guanine phosphoribosyl transferase gene near promoter; | 7, 8 |
| HSP70 origin | Human | Heat shock protein 70 gene promoter; | 29 |
| IGH origin | Mouse | Initiation zone downstream of IgH heavy chain locus; Initiation at upstream region occurs only during pre-B cell development | 35 |
| LMNB2 origin | Human | 0.5 kb downstream of lamin B2 gene; | 3, 6, 23 |
| LYZ origin | Chicken | 3'-end of lysozyme gene; CpG island | 25 |
| MCM4/PRKDC | Human | Dual promoter between the MCMC4 and PRKDC genes | 20 |
| MYC origin | Human | Upstream of promoter region of c-Myc gene; | 32, 13 |
| YWHAH origin | Human | A non-'O'-family, non-Alu homologous sequence within 14-3-3-eta gene; | 26 |
| ORS12 | Monkey | centromeric region containing an α-satellite sequence; | 24 |
| rRNA genes | Human, Mouse Rat | Multiple initiation sites in the 31 kb non transcribed spacer, and a preferred region in promoter; similar to fission yeast | 28, 12, 14, 34, 21 |
| rRNA genes | Frog | Localized to nontranscribed spacer region after mid-blastula transition | 16 |
| RPE origin | Human | Within coding region (exon) of ribulose-5-phosphate-3-epimerase | 1 |

TABLE 1-continued

Replication Origins Mapped in Metazoan Genomes

| Origin | Species | Location and Properties | Refs.* |
|---|---|---|---|
| RSP14 origin | Hamster | OBR within coding region of ribosomal protein S14 | 30 |
| RHO origin | Hamster | Upstream of rhodopsin gene; Initiation zone includes the nontranscribed RHO gene; but not a nearby transcribed gene | 10 |
| TOP1 origin | Human | TOP1 promoter | 17 |
| TK1 origin | Hamster | Promoter region of thymidine kinase gene; CpG island | 9 |

*The first report of origin mapping and, where possible, the most recent report are cited.
1. Altman, A. L. and E. Fanning, Mol Cell Biol, 2004. 24(10): p. 4138-50.
2. Araujo, F. D., et al., J Biol Chem, 1999. 274(14): p. 9335-41.
3. Biamonti, G., et al., Chromosoma, 1992.
4. Burhans, W. C., et al., Cell, 1990. 62(5): p. 955-965.
5. Carroll, S. M., et al., Mol Cell Biol, 1993. 13(5): p. 2971-81.
6. Cohen, S. M., et al., J Cell Biochem, 2002. 85(2): p. 346-56.
7. Cohen, S. M., et al., J Cell Biochem, 2003. 88(5): p. 923-31.
8. Cohen, S. M., et al., Genomics, 2004. 84(3): p. 475-84.
9. Delgado, S., et al., EMBO J, 1998. 17: p. 2426-2435.
10. Dijkwel, P. A., et al., Exp Cell Res, 2000. 256(1): p. 150-7.
11. Dijkwel, P. A., S. Wang, and J. L. Hamlin, Mol Cell Biol, 2002. 22(9): p. 3053-65.
12. Gencheva, M., B. Anachkowa, and G. Russev, J Biol Chem, 1996. 271: p. 2608-2614.
13. Ghosh, M., et al., Mol Cell Biol, 2004. 24(23): p. 10193-207.
14. Gogel, E., et al., Chromosoma, 1996. 104(7): p. 511-8.
15. Heintz, N. H. and J. L. Hamlin, Proc Natl Acad Sci USA, 1982. 79(13): p. 4083-7.
16. Hyrien, O., C. Maric, and M. Mechali, Science, 1995. 270(5238): p. 994-7.
17. Keller, C., et al., J Biol Chem, 2002. 277(35): p. 31430-40.
18. Kelly, R. E., et al., Mol Cell Biol, 1995. 15(8): p. 4136-48.
19. Kitsberg, D., et al., Nature, 1993. 366(6455): p. 588-90.
20. Ladenburger, E. M., C. Keller, and R. Knippers, Mol Cell Biol, 2002. 22: p. 1036-1048.
21. Lebofsky, R. and A. Bensimon, Mol Cell Biol, 2005. 25(15): p. 6789-97.
22. Miyagi, S., et al., Biochem Biophys Res Commun, 2000. 278(3): p. 760-5.
23. Paixao, S., et al., Mol Cell Biol, 2004. 24(7): p. 2958-67.
24. Pelletier, R., et al., J Cell Biochem, 1997. 66(1): p. 87-97.
25. Phi-van, L. and W. H. Stratling, Nucleic Acids Res, 1999. 27(15): p. 3009-17.
26. Price, G. B., et al., J Biol Chem, 2003. 278(22): p. 19649-59.
27. Prioleau, M. N., M. C. Gendron, and O. Hyrien, Mol Cell Biol, 2003. 23(10): p. 3536-49.
28. Sanchez, J. A., S. M. Kim, and J. A. Huberman, Exp Cell Res, 1998. 238(1): p. 220-30.
29. Taira, T., S. M. Iguchi-Ariga, and H. Ariga, Mol Cell Biol, 1994. 14(9): p. 6386-97.
30. Tasheva, E. S. and D. J. Roufa, Mol Cell Biol, 1994. 14(9): p. 5628-35.
31. Virta-Pearlman, V. J., P. H. Gunaratne, and A. C. Chinault, Mol Cell Biol, 1993. 13(10): p. 5931-42.
32. Waltz, S. E., A. A. Trivedi, and M. Leffak, Nucleic Acids Res, 1996. 24(10): p. 1887-94.
33. Wang, L., et al., Mol Cell Biol, 2004. 24(8): p. 3373-86.
34. Yoon, Y., et al., Mol Cell Biol, 1995. 15(5): p. 2482-9.
35. Zhou, J., et al., Proc Natl Acad Sci USA, 2002. 99(21): p. 13693-8

The human β-globin locus resides on chromosome 11 and includes five genes that encode the β-subunit of hemoglobin. Two redundant, independent, and non-overlapping replicator sequences (Rep-P and Rep-I) that dictate initiation of DNA replication from the human β-globin locus are located within the IR region between the δ and β globin genes. Each of the replicators is sufficient to initiate replication at ectopic sites and within each replicator, initiation of DNA replication requires cooperation between at least two unique, non-redundant sequences (Wang et al., *Mol. Cell. Biol.*, 24: 3373-3386, 2004.

The lamin B2 replicator is located in a 1.2 kb region between positions 3691 and 4978 in the sequence encoded by GenBank Accession No. M94363. This fragment comprises the origin of bidirectional DNA replication (OBR), the origin-protected region (OPR), and part of the nearby CpG island. The activity of the lamin B2 replicator critically depends on a 290 bp region containing the OPR and is positively influenced by the nearby CpG island (Paixao et al., *Mol. Cell Biol.*, 24:2958-2967, 2004).

The replicator associated with the chorion gene locus in *Drosophila melanogaster* is composed of two elements: a 320 bp amplification control region 3 (ACE3) and an amplification enhancer region d (AERd), located about 1.5 kb away, that comprises the DNA replication initiation site ori-β (Lu et al., *Genes Dev.*, 15:134-146, 2001; Zhang and Tower, *Development*, 131:2089-2099, 2004).

The replicator associated with Chinese hamster DHFR locus (5.8 kb) requires at least four elements for the initiation of DNA replication at ectopic loci (Altman and Fanning, *Mol. Cell Biol.*, 21: 1098-1110, 2001).

The human c-myc replicator (2.4 kb)) requires several elements (Liu et al., *Mol. Cell Biol.*, 23:1832-1842, 2003).

A metazoan replicator is identified by transferring the putative replicator form its native site to ectopic chromosomal regions and testing for replication initiation at the new location. Replicators that exhibit origin activity at ectopic locations lose this activity when mutations are introduced. In addition, mutant replicators that cannot initiate replication also cannot prevent gene silencing and will replicate late in S phase.

The disclosed method also envisages using replicator variants. Variant replicator sequences may be produced by standard DNA mutagenesis techniques, including without limitation M13 primer mutagenesis. Details of these techniques are provided in Sambrook et al., *Molecular Cloning: A Laboratory Manual*, New York: Cold Spring Harbor Laboratory Press, 1989, Ch. 15. By the use of molecular engineering techniques well known in the art, variants may be created that differ from the replicator nucleic acid sequences disclosed.

DNA molecules and nucleotide sequences that are derivatives of those specifically described herein, and which differ from those disclosed by the deletion, addition, or substitution of nucleotides, while retaining the capability of modulating the timing of DNA replication and influencing chromatin structure, are comprehended by this disclosure. Also comprehended by the method is the use of more closely related nucleic acid molecules that share at least 80%, at least 85%, at least 90%, at least 95%, or at least 98% nucleotide sequence homology with the replicator nucleic acid sequences described herein.

Nucleic acid molecules that are derived from the replicator sequences include molecules that hybridize under stringent conditions to the disclosed replicator nucleic acid sequences, or fragments thereof. Useful hybridization conditions are described above.

VI. Transgene Constructs

The disclosure provides for transgene constructs where the replicator sequence and the coding nucleic acid sequence are placed in any orientation with respect to each other, for example, either downstream (for instance, 3') or upstream (for instance, 5'). In one embodiment, at least one replicator is located downstream (for instance, 3') of the coding nucleic acid sequence. In other embodiments, at least one exogenous replicator is located upstream (for instance, 5') of the coding nucleic acid sequence.

The replicator sequence and the coding nucleic acid sequence may be separated by any number of nucleotides as long as the prevention, delay, or inhibition of silencing of the coding nucleic acid sequence described herein is observed. For example, there may be at least about 2, at least about 5, at least about 10, at least about 20, at least about 50, at least about 100, at least about 250, at least about 500, at least about 1000, at least about 2000 nucleotides separating the replicator sequence and the coding sequence. In other embodiments, there may be at least about 3, 5, 7, 10, 12, 15, 20, 25, 50, 100, 200, or more kb separating the replicator sequence and the coding sequence. Conventional transgene constructs can include up to 15 kb of DNA sequences, but longer sequences (hundreds of kb) can be inserted in mammalian cells via the use of viral vectors, such as adenoviruses, or by creating artificial human chromosomes. In some embodiments, insertions of long sequences are necessary, because replicons are known to encompass up to 400 kb (Ermakova et al., *Mol Cell.* 3 (3):321-30, 1999).

Other sequences can be included in the transgene construct. For example, any regulatory element or sequence encoding a selectable marker can be included in the transgene construct. In one embodiment, the transgene construct includes a promoter sequence. In other embodiments, the transgene construct includes a selectable marker sequence, or both a promoter and a selectable marker sequence.

Nucleic acid sequences encoding any one of a variety of selectable markers can be included in the transgene construct. For example, a sequence encoding a selectable marker which confers a selectable phenotype such as drug resistance, nutritional auxotrophy, resistance to a cytotoxic agent or expression of a surface protein, can be used. Selectable marker genes which can be used include green fluorescent protein (GFP), neomycin, guanine phosphoribosyl transferase (gpt), DHFR, adenosine deaminase (ADA), blasticidin, hygromycin, multidrug resistance-1 (MDR1), and histidinol dehydrogenase (hisD). The selectable phenotype conferred makes it possible to identify and isolate the cells containing the transgene. Selectable markers can be divided into two categories: positive selectable and negative selectable. In positive selection, cells expressing the positive selectable marker are capable of surviving treatment with a selective agent (such as neomycin, gpt, DHFR, ADA, hygromycin, MDR1 and hisD) or can be separated from cells that do not express the selectable marker (GFP). In negative selection, cells expressing the negative selectable marker are destroyed in the presence of the selective agent (for example, thymidine kinase, gpt).

A variety of promoters can be included in the transgene construct. Examples of promoters include, but are not limited to the SV40 promoter, the CMV enhancer-promoter, the CMV enhancer/β-actin promoter, and the tissue-specific promoters β-globin and probasin. Other promoter sequences which can be used to when designing the transgene construct and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

The disclosed transgene constructs contain replicator sequences alone or operably linked with other elements. The elements may be additional cis-acting elements, for example sequences including the locus control region (LCR), AT-rich sequences, matrix attachment sites, CpG islands, or transcriptional control elements.

A replicator nucleic acid sequence can be included in an expression vector operably linked to a coding sequence. Such expression vector may optionally contain auxiliary expression control sequences, including without limitation core promoter sequences, transcription initiators, transcription terminators, a start codon (for instance, ATG) preceding a protein-encoding nucleic acid sequence, splicing signal for introns, maintenance of the correct reading frame of that nucleic acid sequence to permit proper translation of mRNA, and stop codons. Generally, auxiliary expression control sequences will include the minimal sequence sufficient to support transcription.

In certain embodiments, an expression vector includes a nucleic acid sequence encoding a polypeptide of interest (coding nucleic acid sequence). A polypeptide of interest can be a polypeptide that affects a function of the transformed or transfected cell. Polypeptides of interest include, but are not limited to, therapeutic polypeptides. Specific, non-limiting examples of a polypeptide of interest include α-globin, β-globin, adenosine deaminase, Von Willebrand Factor, blood coagulating plasma factors VIII and IX, or ADAMTS13 (a disintegrin and metalloproteinase with thrombospondin repeats). A polypeptide of interest can also be a marker polypeptide, which is used to identify a cell of interest. Marker polypeptides include fluorescent polypeptides, enzymes, or antigens that can be identified using conventional molecular biology procedures. For example, the polypeptide can be a fluorescent marker (for example, green fluorescent protein, *Aequorea victoria*, or *Discosoma* DSRed), an antigenic markers (for example, human growth hormone, human insulin, human HLA antigens), a cell surface marker (for example, CD4, or any cell surface receptor), or an enzymatic marker (for example, lacZ, alkaline phosphatase). Techniques for identifying these markers in host cells include immunohistochemistry, fluorescent-activated cell sorting (FACS), and fluorescent microscopy, and are well known in the art. In other embodiments, the expression vector may include a polylinker (for instance, a multiple cloning site) to permit insertion of a nucleic acid sequence encoding a polypeptide of interest.

RNA molecules transcribed from an expression vector need not always be translated into a polypeptide to express a functional activity. Specific non-limiting examples of other molecules of interest include antisense RNA molecules complementary to an RNA of interest, ribozymes, small inhibitory RNAs, and naturally occurring or modified tRNAs.

Expression vectors including a replicator, alone or operably linked to a coding nucleic acid sequence, can be used to transform host cells. Hosts can include isolated microbial, yeast, insect and mammalian cells, as well as cells located in the organism. Biologically functional viral and plasmid DNA vectors capable of expression and replication in a host are known in the art, and can be used to transfect any cell of interest.

Transfection of a host cell with recombinant nucleic acid molecule may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, transfection of nucleic acid molecules may be achieved by, for example, calcium phosphate co-precipitates, microinjection, electroporation, insertion of a plasmid encased in liposomes, or use of virus vectors. Eukaryotic cells can also be transformed with more than one nucleic acid molecule; thus, for example, a eukaryotic cell may be co-transfected with a construct containing a replicator alone, or operably linked to a promoter and a second foreign nucleic acid molecule encoding a helper protein or a selectable marker. Other useful methods use nucleic acid delivery vehicles derived from viruses, including but not limited to adenoviruses, retroviruses, vaccinia viruses, lentiviruses, and adeno-associated viruses (see, for example, *Eukaryotic Viral Vectors*, Cold Spring Harbor Laboratory Press, Gluzman ed., 1982).

VII. Gene Transfer of a Transgene Construct Containing a Replicator Sequence

Conventional viral and non-viral based gene transfer methods can be used to introduce the transgene constructs disclosed above (that include a replicator nucleic acid sequence, either alone or in combination with a coding nucleic acid sequence) in mammalian cells or target tissues (see for example, U.S. Pat. Nos. 6,846,676, 6,537,542, 6,933,113 and U.S. Patent Application No. US20040132683). Such methods can be used to administer the disclosed constructs to cells in vitro. In one embodiment, the disclosed construct is administered for in vivo or ex vivo gene therapy uses. Non-viral vector systems to deliver the disclosed transgene constructs include DNA plasmids, naked nucleic acid, and nucleic acid complexed with a delivery vehicle such as a liposome. Viral vector delivery systems include DNA and RNA viruses, which have either episomal or integrated genomes after delivery to the cell. The transgene construct can be integrated into the genome of a cell, for instance a somatic cell or a germ cell of an organism.

Methods of non-viral delivery of the disclosed transgene constructs include lipofection, microinjection, biolistics, virosomes, liposomes, immunoliposomes, polycation or lipid:nucleic acid conjugates, naked DNA, artificial virions, and agent-enhanced uptake of DNA. Lipofection is described in for example, U.S. Pat. Nos. 5,049,386, 4,946,787; and 4,897,355 and lipofection reagents are sold commercially (for example, Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of the disclosed transgene constructs takes advantage of highly evolved processes for targeting a virus to specific cells in the body and trafficking the viral payload to the nucleus. Viral vectors can be administered directly to the subject (in vivo) or they can be used to treat cells in vitro and the modified cells are then administered to a subject (ex vivo). Conventional viral based gene transfer systems for the delivery of a nucleic acid construct encoding a replicator, either alone or in combination with a transgene, include retroviral, lentiviral, adenoviral, adeno-associated, and herpes simplex virus vectors. Viral vectors are currently the most efficient and versatile method of gene transfer in target cells and tissues. Integration in the host genome is possible with the retrovirus, lentivirus, and adeno-associated virus gene transfer methods. Additionally, high transduction efficiencies have been observed in many different cell types and target tissues.

The sequence of a retrovirus can be altered by incorporating foreign envelope proteins, thereby expanding the potential population of target cells. Lentiviral vectors are members of a class of retroviral vector that is able to transduce or infect non-dividing cells and typically produce high viral titers. Selection of a retroviral gene transfer system would therefore depend on the type of target tissue. Retroviral vectors are comprised of cis-acting long terminal repeats (LTRs) with packaging capacity for up to 6-10 kb of foreign sequence. The minimum cis-acting LTRs are sufficient for replication and packaging of the vectors, which are then used to integrate the therapeutic transgene into the target cell. Widely used retroviral vectors include those based upon murine leukemia virus (MuLV), gibbon ape leukemia virus (GaLV), Simian Immuno deficiency virus (SIV), human immuno deficiency virus (HIV), and combinations thereof. Construction of recombinant lentiviral vectors is well known to those of skill in the art (Zufferey et al., *J. Virol.*, 72:9873-9880, 1998; Lois et al., *Science*, 295, 868-872, 2002).

In other embodiments, an adenoviral based system is used. Adenoviral based vectors are capable of very high transduction efficiency in many cell types and do not require cell division. This vector can be produced in large quantities in a relatively simple system. Adeno-associated virus ("AAV") vectors are also used to transduce cells with target nucleic acids, for example, in the in vitro production of nucleic acids and peptides, and for in vivo and ex vivo gene therapy procedures. Construction of recombinant AAV vectors is well known to those of skill in the art (Flotte et al. *Proc. Natl. Acad. Sci. USA*, 90:10613-10617, 1993; Snyder et al., *Nature Med.*, 5:64-70, 1999; Chatterjee et al., *Blood*, 93:1882-1894, 1999).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be produced at high titer and they readily infect a number of different cell types. Ad vectors can transduce multiple types of tissues in vivo, including non-dividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and psi.2 cells or PA317 cells, which package retrovirus. Viral vectors used in gene transfer are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line.

Transgene constructs can be delivered in vivo by administration to a subject, typically by systemic administration (for example, intravenous, intraperitoneal, intramuscular, subdermal, or intracranial infusion) or topical application, as described below. Alternatively, constructs can be delivered to cells ex vivo, such as cells explanted from a subject (for example, lymphocytes, bone marrow aspirates, tissue biopsy) or universal donor hematopoietic stem cells, followed by reimplantation of the cells into a subject, usually after selection for cells which have incorporated the vector.

Ex vivo cell transfection for diagnostics, research, or for gene transfer (for example, via re-infusion of the transfected cells into the host organism) is well known to those of skill in the art. In one embodiment, cells are isolated from the subject, transfected with the disclosed constructs, and re-infused back into the subject. Various cell types suitable for ex vivo transfection are well known to those of skill in the art. In one embodiment, stem cells, such as embryonic stem cells, are used in ex vivo procedures for cell transfection and gene transfer. The advantage to using stem cells is that they can be differentiated into other cell types in vitro, or can be introduced into a subject where they will engraft in the bone marrow. Methods for differentiating CD34+ cells in vitro into clinically important immune cell types using cytokines such a GM-CSF, IFN-gamma and TNF-alpha are well known.

Stem cells are isolated for transduction and differentiation using known methods. For example, hematopoietic or erythroid stem cells are isolated from other bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells).

Viral vectors (for example, retroviruses, lentiviruses, adenoviruses, liposomes, etc.) containing the disclosed constructs, also can be administered directly to the organism for transduction of cells in vivo. Alternatively, naked DNA can be administered.

Viral vectors containing the disclosed transgene constructs, can be administered directly to the patient for modulation of gene expression and for therapeutic or prophylactic applications directed against, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Administration of therapeutically effective amounts is by any of the routes normally used for introducing transgene constructs into the tissue to be treated. The vectors are administered in any suitable manner, preferably with pharmaceutically acceptable carriers. Suitable methods of administering such vectors are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, for example, *Remington's Pharmaceutical Sciences*, 17$^{th}$ ed. 1985)).

The vectors including the disclosed constructs can be made into aerosol formulations (for instance, they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The invention is illustrated by the following non-limiting Examples.

EXAMPLES

Example 1

Human Replicators Can Prevent Gene Silencing and Maintain Early Replicating Chromatin This example describes a non-limiting method of preventing gene silencing and maintaining early replication of chromatin. At least some portion of the subject matter in this Example is disclosed in Fu et al., *Nat. Biotechnol.*, 24:572-576, 2006.

Plasmids

Rep-P (positions 59882-62187 of GenBank Accession Number U01317.1; SEQ ID NO: 2) and mutated Rep-P (Rep-P including a deletion of the AG-rich region at positions 62074-62118 of GenBank Accession Number U01317.1; SEQ ID NO: 32) from the human β-globin locus were described previously (Wang et al., *Mol Cell Biol* 24:3373, 2004). Human lamin B2 (LMNB2) replicator (Paixao et al., *Mol Cell Biol* 24:2958, 2004) (positions 3691 to 4978; GenBank Accession No. M94363) was obtained from genomic DNA of K562 cells by polymerase chain reaction (PCR) amplification with specific primers. All sequences were verified by DNA sequencing at the National Cancer Institute core facility. Replicator sequences were inserted into the HS432-

β-promoter-enhanced green fluorescent protein (GFP) plasmid (Feng et al., *Mol Cell Biol* 21:298, 2001) using standard methodology.

Cell Culture and Transfections

MEL cells harboring plasmids described in FIG. 1 were grown in Dulbecco modified Eagle's medium (Invitrogen) supplemented with 10% heat-inactivated fetal calf serum. Cre recombinase-mediated cassette exchange was performed as previously described (Feng et al., *Mol Cell Biol* 21:298, 2001) with the following modifications. The target MEL cells containing the CMV-HYTK cassette flanked by L1-1L Lox sites inserted at RL4 (integrated into a site on murine chromosome 15) were cotransfected by lipofectamine 2000 (Invitrogen) with 4 μg of a Cre expression plasmid and 4 μg of an exchange plasmid containing the cassette of interest. Clones having lost the HYTK cassette were selected with 10 nM gancyclovir. Replacement of the HYTK cassette by the cassette present in the exchange plasmid was then verified by PCR.

FACS Analysis

GFP expression of the transgenes was monitored by FACS. At least three colonies for each inserted direction were tested every two to four weeks until all colonies were either completely silenced, or up to 6 months. Dead cells were gated out on the basis of morphological parameters (FSC and SSC) and propidium iodide exclusion. The percentage of cells expressing the GFP transgene was estimated using untransfected MEL cells as negative control.

Replication Initiation Analyses

Genomic DNA and nascent-strand DNA were prepared as described previously (Aladjem et al., *Mol Cell Biol* 22:442, 2002). Briefly, DNA was collected from asynchronous cultures and denatured by boiling followed by rapid cooling, and short DNA strands were fractionated by size on neutral sucrose gradients. DNA strands ranging from 0.6 to 2.5 kb were collected and treated with λ exonuclease (Bielinsky et al., *Science* 279:95, 1998; Kobayashi et al., *Mol Cell Biol* 18:3266, 1998). Nascent strands were amplified by real-time PCR in an ABI 7900 thermocycler (Applied Biosystems International) using a series of probe-primer combinations (see Table 2, below) surrounding the inserted replicator and adjacent sequences. The amount of DNA in each sample was quantified by OligoGreen analysis (Molecular Probes, Eugene, Oreg.). Genomic DNA that was not treated with exonuclease was used as a standard for calculating the number of molecules in the template.

Genomic DNA from MEL cells was used as a nontemplate control to verify that primers used in the study were specific for the inserted DNA. To verify that the exonuclease treatment eliminated sequences that are not involved in initiating DNA replication, origin-proximal and origin-distal primer-probe combinations from the host genome were included in each nascent-strand analysis. Data from three PCR reactions for each primer-probe combination were used to calculate the amount of sequence-specific nascent strands using the methods described in Wang et al., *Mol Cell Biol* 24:3373, 2004.

Replication Timing Analyses

Replication timing analyses were performed as described previously (Lin et al., *Curr Biol* 13:1019, 2003) with the following modifications: cells were labeled with BrdU for 90 minutes and with 20 mg/mL Hoechst 33342 dye (Molecular Probes) for 30 minutes before harvesting. Cell cycle fractions were sorted using a Vantage fluorescence-activated cell sorter or elutriator. Newly replicated, BrdU-substituted DNA was isolated by immunoprecipitation with anti-BrdU antibodies as described (Lin et al., *Curr Biol* 13:1019, 2003). Each sample was subject to two sequential rounds of immunoprecipitation, washes, and DNA purification. BrdU-incorporated *Drosophila* genomic DNA was added as an internal control to each sample before immunoprecipitation. The quantity of newly replicated (BrdU-substituted) DNA was determined with OligoGreen and the abundance of mitochondrial DNA sequences (mMT primers) was used to verify that each fraction contained similar quantities of amplifiable DNA strands. Samples containing 8 ng DNA were amplified with a series of primer-probe combinations (see Table 2, below) and analyzed by real-time PCR on an ABI 7900. The quantity of an amplified sequence was calculated using genomic DNA standards with a standard curve from 0.005 to 50 ng per reaction. Each measurement was performed in triplicate. Experiments were performed using each cell line. The relative abundance for each probe-primer combination was calculated as percentage of the number of molecules amplified from a specific cell cycle fraction divided by the number of molecules amplified from the cell cycle fraction where amplification was maximal.

Chromatin Immunoprecipitation (ChIP) Assay

ChIP assays were carried out as described previously (Lin et al., *Curr Biol* 13:1019, 2003) with the following modifications: at 25° C., 4 to 6×10$^7$ MEL cells were fixed for 5 minutes by the addition of 1% formaldehyde to the growth medium. After a series of washings, cells were sonicated six times (for 20 seconds at 1 minute intervals) with a 2-mm tip of a Sonics & Materials (Danbury, Conn.) sonicator at the maximum setting. After centrifugation at 14,000 rpm for 20 minutes, the cleared supernatant was adjusted to contain 1×RIPA buffer (10 mM Tris-Cl pH 8.0, 150 mM NaCl, 1% Triton X-100, 0.1% SDS, 1 mM EDTA, 1 mM phenylmethylfulfonyl fluoride, 1% of a standard protease inhibitor cocktail; Sigma). To reduce nonspecific binding to protein A, chromatin was precleared with 100 μL UltroLink immobilized protein A (50% slurry in RIPA buffer; Pierce, Rockford, Ill.) for 1 hour at 4° C. with rotation. A solution of precleared chromatin (0.5 mL) was incubated with or without 5 μg antibody and rotated at 4° C. for 12 to 16 hours. Antibodies used included anti-acetyl-histone H 3 (#06-599; Upstate Biotechnology, Lake Placid, N.Y.), anti-acetyl-histone H4 (#06-866; Upstate Biotechnology, Lake Placid, N.Y.), anti-dimethyl-histone H3 (Lys 4) (#07-030; Upstate Biotechnology, Lake Placid, N.Y.).

Protein A beads (50 μL) were added to the ChIP mixture and the mixture was incubated for 2 to 4 hours. The protein A beads were then washed once with 1×RIPA buffer, 3 times with 1×RIPA plus 0.5 M NaCl, twice with a Tris-LiCl buffer (10 mM Tris-Cl pH 8.0, 0.25 M LiCl, 1% NP40, 1% deoxycholate, 1 mM EDTA), and twice with TE (10 mM Tris-Cl pH 8.0, 1 mM EDTA). A volume of 0.5 mL of elution buffer (10 mM Tris-Cl pH 8.0, 200 mM NaC 1, 0.5% SDS, 1 mM EDTA) was then added to the washed protein A beads and this mixture was incubated at 65° C. for 12 to 14 hours, followed by treatment with RNase and proteinase K. The DNA was then extracted with phenol-chloroform, precipitated, and resuspended in distilled water. The DNA concentration of the samples was determined by Pico green fluorescence (Molecular Probes). Real-time PCR was used to amplify the ChIP-enriched DNA. The sequences of primers and probes are listed in Table 2.

TABLE 2

Primers and probes used in this study.

| Name | GenBank accession #/ mouse Ch location | Forward primer | Reverse primer | Probe* |
|---|---|---|---|---|
| bG59.8 | Human globin locus (U01317.1) | TGGAAAAGCAAC CCCTGC (SEQ ID NO: 8) | AACTATGGAT CCTTCTCTTG TGTTGG (SEQ ID NO: 16) | GCTGCAGATACC ATCATCCTGGCT TCAA (SEQ ID NO: 24) |
| bG61.3 | Human globin locus (U01317.1) | ACAGAGGCTTTT TGTTCCCCC (SEQ ID NO: 9) | GGTAATCAGT GGTGTCAAAT AGGAGG (SEQ ID NO: 17) | GACACTCTTGCA GATTAGTCCAGG CAGA (SEQ ID NO: 25) |
| bG63.5 | Human globin locus (U01317.1) | GGACAGCAAGAA AGCGAGCT (SEQ ID NO: 33) | TCAGAAAGTG GTGGCTGGTG (SEQ ID NO: 35) | GCTAATGCCCTG GCCCACAAGTAT CACT (SEQ ID NO: 37) |
| bG65.3 | Human globin locus (U01317.1) | TGAGTAATAGTT TCCTGATTCTCC CA (SEQ ID NO: 34) | AAAGTCACTC TCATGGAAAC AGACA (SEQ ID NO: 36) | CCCCAACCCCTG GAAACCATACCT C (SEQ ID NO: 38) |
| bGPro | human beta globin promoter (U01317) | TGAGGGTTTGAA GTCCAACTCC (SEQ ID NO: 10) | GGTCTAAGTG ATGACAGCCG TACC (SEQ ID NO: 18) | AAGCCAGTGCCA GAAGAGCCAAGG A (SEQ ID NO: 26) |
| GFP | GFP coding sequence (U76561) | AGCAAAGACCCC AACGAGAA (SEQ ID NO: 11) | GGCGGCGGTC ACGAA (SEQ ID NO: 19) | CGCGATCACATG GTCCTGCTGG (SEQ ID NO: 27) |
| MCh15 | RL4 site (mCh15.98386944) | TCCGTCCCCTTC TCCTCC (SEQ ID NO: 12) | TTCAGGTTCCA TTGCCACG (SEQ ID NO: 20) | CACCATTCACAC AGCCCACGAGCA (SEQ ID NO: 28) |
| LMNB2 | Human lamin B2 (M94363) | TGGGACCCTGCC CTTTTT (SEQ ID NO: 13) | CGTGACGAAGA GTCAGCT (SEQ ID NO: 21) | TTCTAGTGAGCC TCCGAC (SEQ ID NO: 29) |
| m5'bG | murine beta globin, beta major (X14061) | CCAGCCTCAGTG AGCTCCA (SEQ ID NO: 14) | CCCATCAGACT CACCCTGAAG (SEQ ID NO: 22) | TGTGACAAGCTG CATGTGGATCCT GA (SEQ ID NO: 30) |
| mAmy | murine amylase 2 (M16540) | TCATATTCTAA TCAAGACTAGT GACTTTAGAGC (SEQ ID NO: 15) | TGCCACAACTA CCAATCCTTTT (SEQ ID NO: 23) | CAACTTCATTTC ACACATGACTTT GCTGAGAAA (SEQ ID NO: 31) |

*Probes were labeled 5' with FAM or VIC, and 3' with TAMRA.

Results

Replication Delay Precedes Transcriptional Silencing

The relationship between replication timing and gene silencing was investigated in a mammalian experimental system in which the timing of DNA replication can be altered in a controlled manner (Lin et al., Curr Biol 13:1019, 2003). Recombinase-mediated cassette exchange (RMCE), a method based on site-specific recombination, was used to create isogenic cell lines that vary only in the DNA sequence of a single, constant genomic location. This is important for replication studies because chromosomal locations, differentiation, and changes in cellular metabolism all may affect the timing of DNA replication during S-phase.

It has been previously shown that insertion of an antibiotic resistance marker into a late-replicating site on murine chromosome 15 (random locus 4 or RL4) advances replication timing (Lin et al., Curr Biol 13:1019, 2003). This change in replication timing was reversible: replication could be delayed by replacing the transgene with a cassette that comprised the hypersensitive sites 2, 3, and 4 from the LCR (HS432, also called miniLCR) in the human β-globin locus fused to a green fluorescent protein (GFP) marker (FIG. 1B and FIG. 1C). The replication delay was orientation specific, it correlated with a condensed chromatin conformation, and transgene expression was silenced (Lin et al., Curr Biol 13:1019, 2003; Feng et al., Mol Cell Biol 21:298 2001). These changes did not occur in the absence of the miniLCR (Feng et al., Mol Cell Biol 25, 3864, 2005), suggesting that LCR plays a role as a silencer.

Figure 2C:
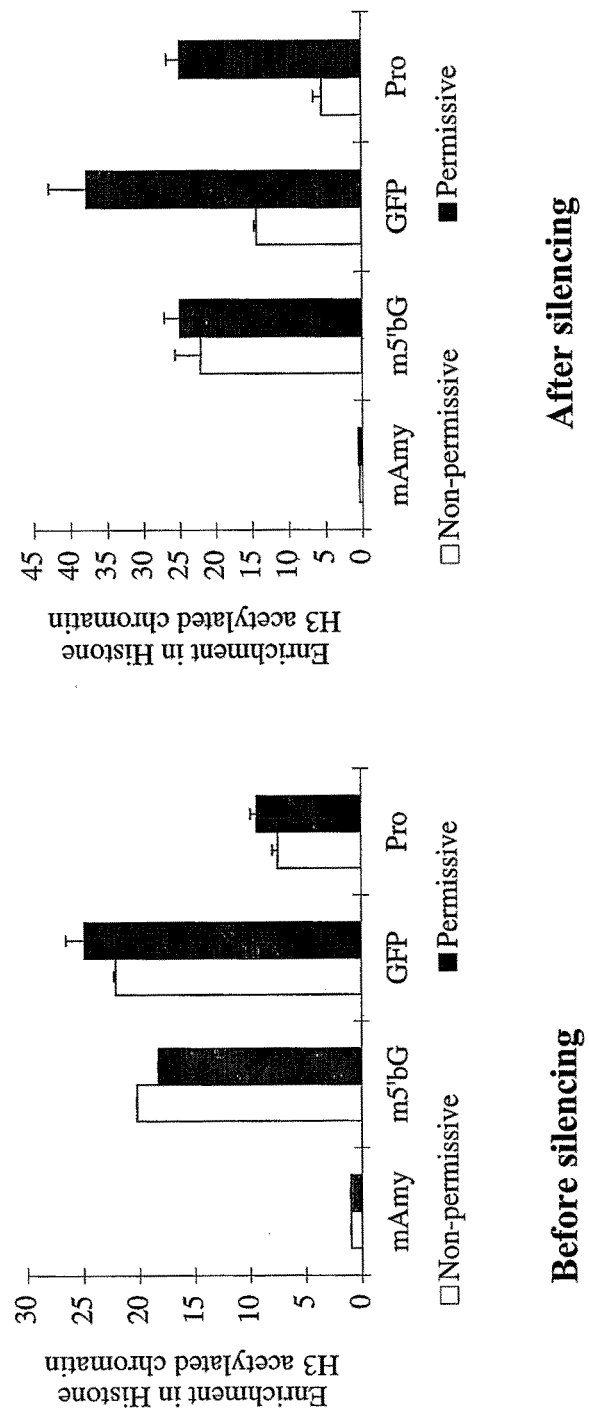
FIG. 2C is a series of graphs representing chromatin immunoprecipitation analysis of chromatin isolated in cells inserted with the miniLCR-pro-GFP-HS4 cassette in the silencing prone and permissive orientations at different times after transfection. Chromatin was isolated with antibodies against acetylated histone H3 and analyzed by real-time PCR. Primers and probes include m5'bG, murine β-globin sequences, which replicate early in MEL cells; mAmy, murine amylase, which replicates late; GFP and Pro are sequences from the transgene, which is sequence from the transgene inserted into murine chromosome 15 (see FIG. 1 for details).

To determine whether transcriptional silencing occurred before the transition to late replication, cell lines containing an integrated transgene cassette that included the mini-LCR and a β-globin promoter driving the expression of GFP was used (FIGS. 1B and 1C, construct I). As described above, this cassette undergoes orientation specific gene silencing. The transgene also contained a second copy of the HS4 putative insulator (HS4) at the 3' end; the insertion of the additional copy of HS4 did not prevent transcriptional silencing but slowed the silencing process, which typically was complete within three weeks. With the HS4-containing construct, almost all cells expressed GFP three weeks after transfection, and silencing was observed five weeks later (FIG. 2A).

Replication timing was measured by determining the abundance of transgene sequences in BrdU-substituted DNA obtained from cells at different stages of the cell cycle. Transgene sequences replicated late in S-phase 3 weeks after transfection (about 5 weeks before silencing—FIG. 2B). Five weeks after transfection, transgene sequences were abundant in chromatin containing acetylated histone H3 (FIG. 2C) and the abundance of transgene sequences in chromatin containing acetylated histone H3 had progressively declined during the silencing process. These data indicated that the chromatin acetylation status correlated with the transcriptional status of the transgene whereas the replication delay preceded silencing and histone deacetylation. Hence, replication delay was not a consequence of a lack of transcription. Although the cell number was not sufficient to perform a replication timing assay earlier than 3 weeks after transfection, it is likely that the replication delay occurred shortly after insertion of the transgenes.

Functional Replicators Prevent Replication Delay

Previous findings showed that transgenes that include only the LCR hypersensitive sites, the globin promoter, and the GFP marker do not initiate DNA replication (Lin et al., *Curr Biol* 13:1019, 2003). To determine whether the insertion (that is, integration) site on murine chromosome 15 contains sequences that prohibit initiation of DNA replication, replicator sequences were included in transgenes that contained the LCR sequences. The entire globin IR (SEQ ID NO: 1) and Rep-P (SEQ ID NO: 2), a shorter replicator derived from the human β-globin IR, which functions as an initiation site in the native locus and can initiate replication when transferred to ectopic sites (Aladjem et al., *Science* 281:1005, 1998), was integrated first (FIG. 1C; constructs III and IV). As a control, a dysfunctional variant of Rep-P (FIG. 1C construct V) was generated in which a 45-bp region, known to be essential for replicator activity, was mutated (Wang et al., *Mol Cell Biol* 24:3373, 2004). Lamin B2 replicator (FIG. 1C; construct VI), derived from the region between the human lamin B2 (LMNB2) and TIMM13 genes and which was shown to initiate replication at ectopic sites, was also used (Paixao et al., *Mol Cell Biol* 24:2958, 2004).

Figure 3A:
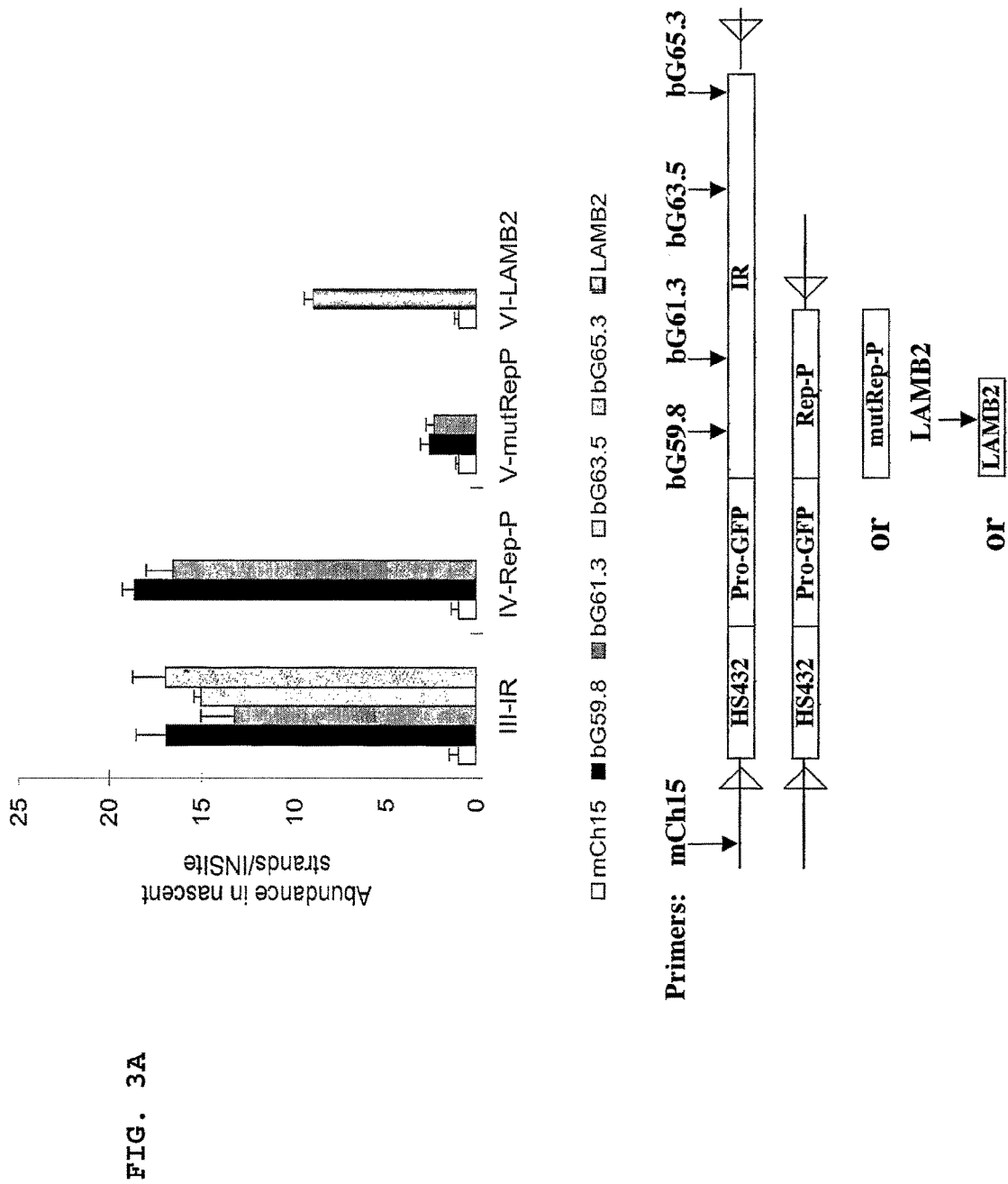
FIG. 3A is a graph showing the initiation of DNA replication from the transgene inserted at RL4, as tested by the nascent-strand abundance assay. The transgenes included the entire IR (FIG. 1C, construct III), Rep-P (FIG. 1C, construct IV), LAMB2 (Lamin B2 from the LMNB2 locus) (FIG. 1C, construct VI) or mutRep-P, in which a 45 basepair sequence essential for initiation was mutated (FIG. 1C, construct V). The abundance of the nascent strands in the transgene was tested by real-time PCR. Primers and probes include MCh15, which is genomic DNA of the RL4 region, previously shown to exhibit no DNA replication initiation (Lin et al., *Curr Biol* 13:1019, 2003), and bG59.8, bG61.3, bG63.5, and bG65.3, which are from the 8 kb IR of the β-globin locus (Wang et al., *Mol Cell Biol* 24:3373, 2004). Replication activity was the relative enrichment of the specific gene to the MCh15.

It was determined whether replication initiated within the replicator-containing transgenes by isolating short, nascent DNA strands from asynchronously replicating cells, based on their size (600-1500 bases) and their ability to withstand lambda exonuclease treatment, which does not digest RNA-primed DNA. Replication initiated in transgenes that contained the entire IR, intact Rep-P, and LMNB2 replicators, but not the mutated Rep-P (FIG. 3A). Replication initiated within Rep-P when inserted in constructs having either of two orientations: the silent orientation, in which LCR-GFP combinations can delay replication, and the transcription-permissive orientation, in which the same transgene does not alter replication timing.

Figure 3B:
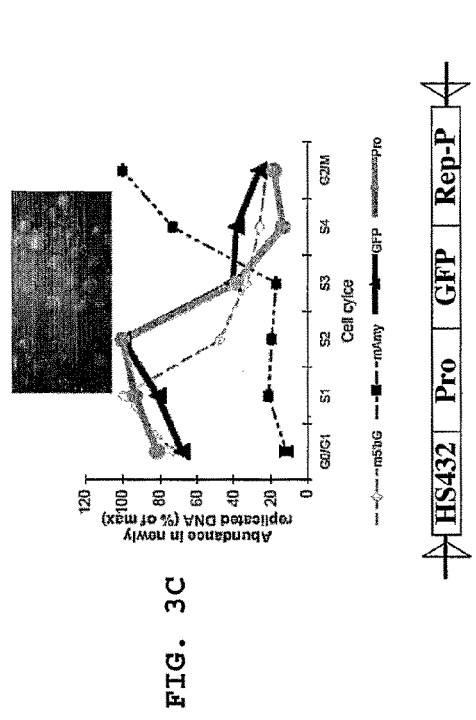
FIGS. 3B-E are a series of graphs showing replication timing and GFP expression of the transgenes inserted at the silencing-prone orientation at the RL4 site.
Figure 3C:
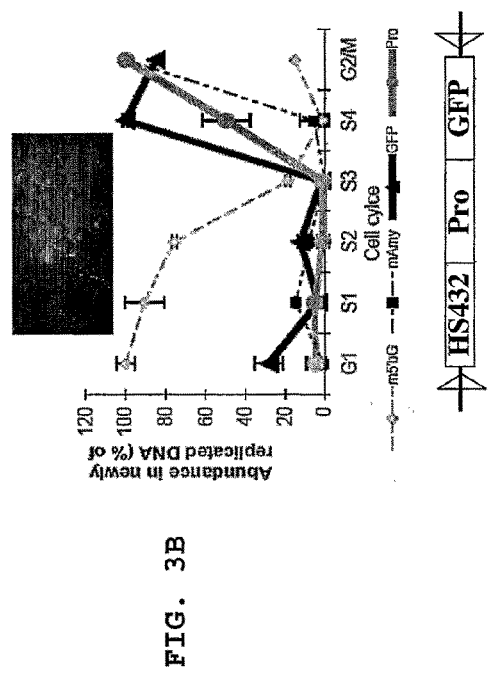
Figure 3D:
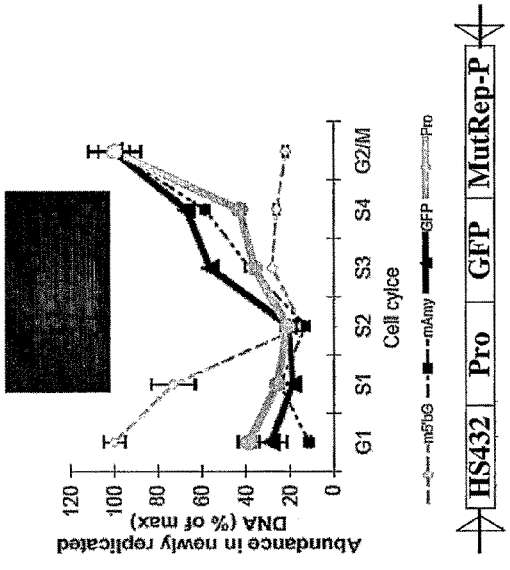
Figure 3E:
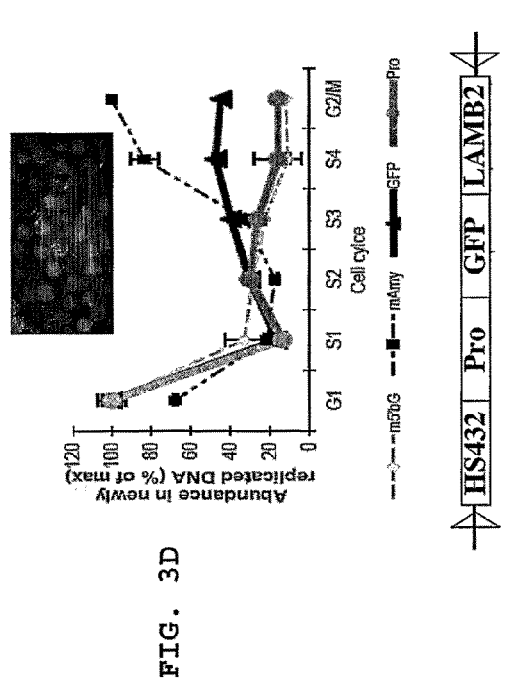
Figures 5A, 5B:
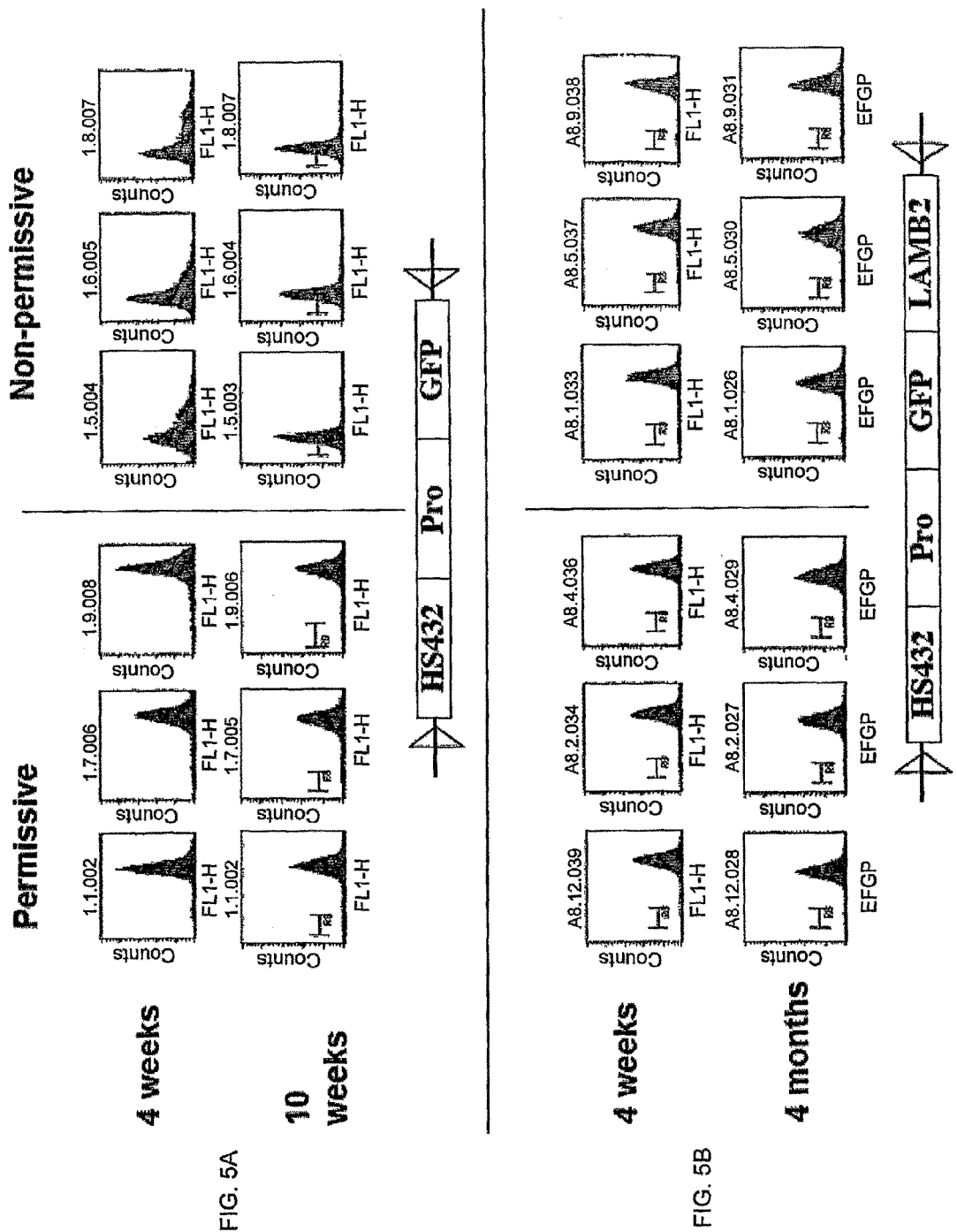
FIG. 5A is a series of graphs illustrating GFP expression in the transgene without a replicator. GFP expression was orientation dependent. When the transgene was inserted into the silencing-prone orientation, cells exhibited a decrease in GFP expression 4 weeks after transfection, and no GFP was detected at 10 weeks. No gene silencing was observed in the permissive orientation.
FIG. 5B is a series of graphs illustrating GFP expression in the transgene with a replicator (LMNB2). GFP expression was stable in both the permissive orientation and the silencing-prone orientation 4 months after transfection. Scale: X-axis is log scale ($10^0$ to $10^4$); Y-axis is linear (0 to 200).

The expression status and replication timing of replicator-containing and replicator-deficient transgenes that were inserted in the silencing-prone orientation was then compared. As shown in FIG. 3B, when transgene I was inserted in the silencing-prone orientation, GFP expression was silenced and replication was delayed. By contrast, a transgene that contained Rep-P (transgene IV) replicated early (FIG. 3C). Importantly, although this transgene was inserted in the same silencing-prone orientation as transgene I, it exhibited stable GFP expression for longer than a year. An insertion of the entire IR (transgene III) and LMNB2 (transgene VI; FIG. 3D) also prevented replication delay and exhibited stable expression. These data indicate that inclusion of functional replicators in the transgene prevented replication delay and gene silencing. Importantly, replication occurred in late S-phase and gene expression was silenced in cells containing the mutated Rep-P (transgene V; FIG. 3E), which did not initiate DNA replication. These observations indicate that a functional replicator is required to prevent replication delay and gene silencing of transgene constructs integrated into the genome of a cell. The prevention of gene silencing by replicators was observed in multiple clones derived from independent transfections (FIG. 5).

The timing of DNA replication of replicator-containing transgenes that were inserted in the silencing-prone orientation was then determined. Replication timing was determined by analyzing the abundance of BrdU-substituted newly replicated DNA from cells fractionated according to their cell cycle stages. Primers from transgene I preferentially amplified sequences from BrdU-substituted DNA from late S-phase but did not amplify transgene sequences from BrdU-substituted DNA from early S-phase fractions. These data suggested that transgene I, which did not contain a replicator, replicated late (FIG. 3B).

By contrast transgene IV, which contained Rep-P, replicated early during S-phase (FIG. 3C). An insertion of the entire IR and LAMB (FIG. 3D; FIG. 1C; construct VI) also prevented replication delay. These data suggested that the inclusion of a functional replicator in the transgene prevented the replication delay when the transgene construct was integrated into the genome of the cell.

Replication occurred in late S-phase in cells containing the mutated Rep-P (FIG. 3E; FIG. 1C; construct V), which did not initiate DNA replication, suggesting that a dysfunctional replicator did not prevent replication delay (or inhibit silencing). As controls, it was verified that the murine β-globin locus, an early-replicating locus in MEL cells, replicated early in all the tested cells and that the murine amylase locus, a late-replicating locus, replicated late in both orientations. These findings further confirmed that insertion of a replicator sequence could affect the timing of DNA replication in the vicinity of the insertion site and did not affect global patterns of DNA replication in the host cells.

Functional Replicators Prevent Chromatin Condensation

Figure 4:
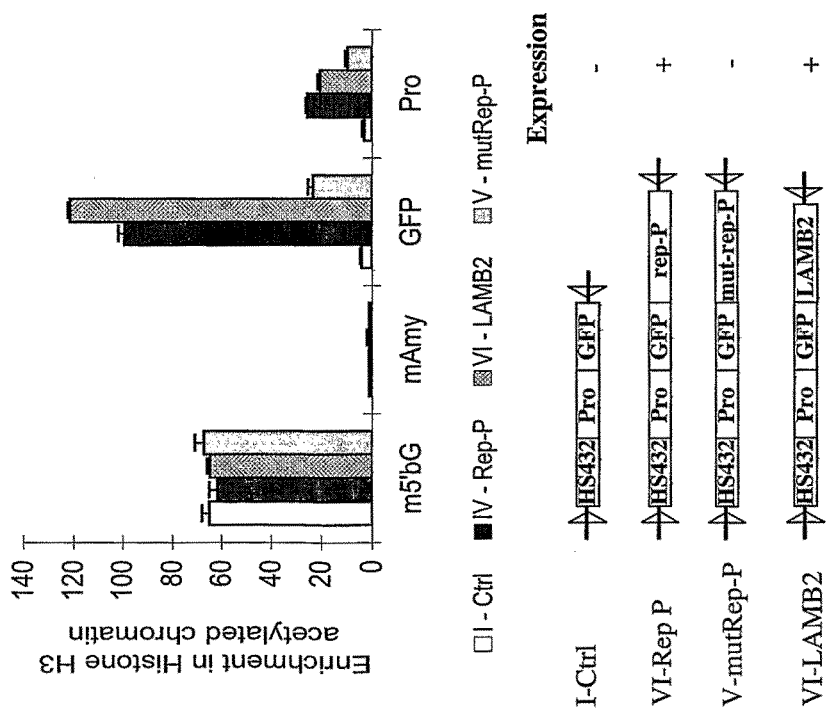
FIG. 4 is a graph illustrating that replicators can prevent chromatin condensation at the RL4 site. A chromatin immunoprecipitation (ChIP) assay with antiacetylated histone H3 antibody was performed to determine whether initiation of DNA replication within the transgene affects LCR-mediated chromatin condensation. Specific transgene and host sequences in the chromatin-immunoprecipitated DNA were detected by real-time PCR. The enrichment of the transgenes and host genes in the chromatin immunoprecipitated by antiacetylated histone H3 antibody was calculated as the ratio of chromatin-immunoprecipitated DNA to input genomic DNA and was normalized by murine amylase (see FIGS. 2 and 3 for details of specific transgene and host sequences). Transgene construct designations correspond to FIG. 1C.

To determine whether the initiation of DNA replication within the transgene affected chromatin condensation, ChIP analysis was performed with antibodies against acetylated or methylated histones, and the enrichment of specific sequences in the precipitated chromatin fraction was measured by real-time PCR (Lin et al., *Curr Biol* 13:1019, 2003). No enrichment of the transgene by anti-acetylated histone H3 antibody was observed in chromatin of cells harboring construct I (lacking a replicator) in the silencing prone orientation (FIG. 4). However, when cells were transfected at the silencing-prone orientation with constructs that contained the functional replicators Rep-P (construct IV) and LMNB2 (construct VI), but not the mutated Rep-P (construct V), transgene-specific sequences were enriched in chromatin containing acetylated histone H3 (FIG. 4).

Similar data were obtained when chromatin condensation was tested for using antibodies against acetylated histone H4 or methylated histone H3, lys4. As a control, acetylation of histone H3 was not detected at the murine amylase locus, which is not transcribed in MEL cells, but was detected in sequence from the murine β-globin locus, which is transcribed in these cells (Forsberg et al., *Proc Natl Acad Sci USA* 97:14494, 2000). All the transgenes exhibited decondensed chromatin when the transgene was inserted at RL4 in the opposite, transcription-permissive orientation. These findings suggested that the presence of a replicator prevents histone deacetylation.

Transgene Insertions at Random Locus 5 (RL5)

Figure 6A:
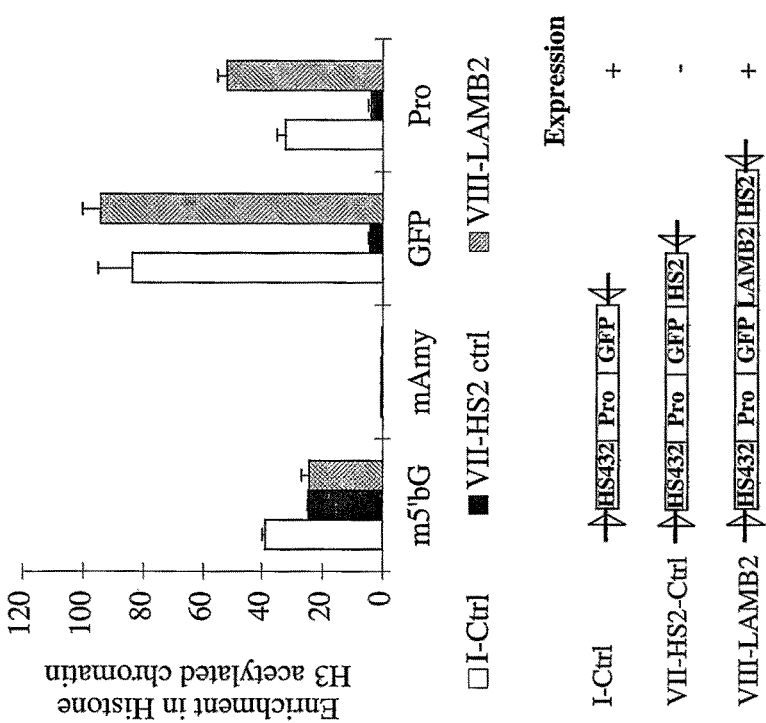
FIG. 6A is a CHIP assay with antiacetylated histone H3 antibodies using primers from the indicated transgenes.
Figure 6B:
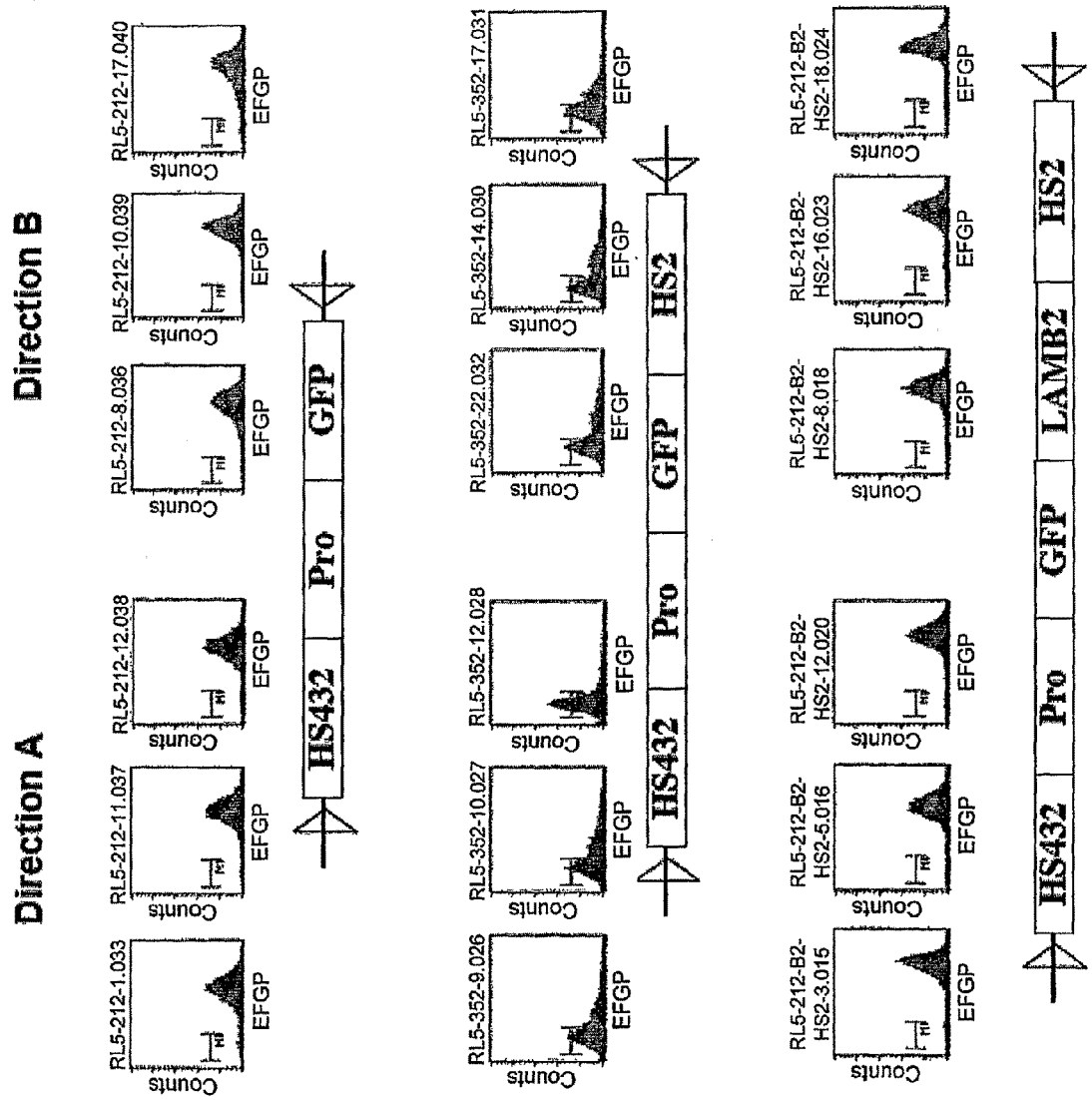
FIG. 6B is a series of graphs illustrating that GFP gene expression of the transgene with/without replicator, as monitored by FACS, at 10 weeks after transfection at the RL5 site. Gene expression at RL5 was not orientation-dependent; transgene directions were therefore arbitrarily referred to as Orientation A (Direction A) and Orientation B (Direction B). GFP expression from a transgene that contained LCR sequences (HS432) linked to the promoter-GFP cassette was stable in both orientations; by contrast, GFP expression was silenced in both orientations when a second copy of the HS2 from the LCR was added at the 3' end of the expression cassette. Silencing was prevented and GFP expression was stable when a replicator sequence was added to the cassette flanked by the LCR and HS2. Scale: X-axis is log scale ($10^0$ to $10^4$); Y-axis is linear (0 to 200).

All the studies reported above were performed on transgenes inserted into a single, constant genomic site located on murine chromosome 15. To determine whether replicators can prevent gene silencing at other locations, a set of transgene insertions at another site, random locus 5 (RL5; located on murine chromosome 4) was created. Most transgenes inserted into RL5 retain expression in both orientations. However, a transgene containing a second copy of hypersensitive site 2 (HS2; construct VII) exhibited silencing (FIG. 6A). When a functional replicator (LMNB2) was inserted into the transgene at the RL5 site (construct VIII), the integrated replicator-containing transgene maintained stable expression in both orientations for at least 4 months (FIG. 6A). Transgenes that contained replicator sequences were enriched in chromatin containing acetylated histone H3, whereas transgenes that did not contain replicators, but contained HS2, were not (FIG. 6B). These data demonstrate that replicators can prevent gene silencing and histone deacetylation at the RL5 site when integrated into the genome of the cell. Thus, the effects of replicators on gene expression and chromatin structure are not limited to the RL4 site.

Discussion

The major finding in this work is that either of two functional replicators from two unlinked human loci were able to (1) prevent gene silencing, (2) prevent replication delay, and (3) prevent chromatin condensation when included in transgenes that typically undergo gene silencing. These two replicators do not share specific consensus sequences but do share some sequence features such as a series of AT stretches near a relatively GC-rich region (Aladjem et al., *EMBO Rep* 5:686, 2004).

A variant replicator sequence that did not initiate DNA replication also did not prevent gene silencing and replication delay. These observations suggest that the ability to maintain early replicating chromatin and prevent chromatin condensation is linked to replicator activity which unexpectedly provides silencing inhibition.

At the human β-globin locus, LCR is essential for initiation of DNA replication and is required for early replication in erythroid cells (Kim et al., *Genes Dev* 6:928, 1992), but this requirement for LCR is not preserved at ectopic locations: in early-replicating ectopic sites, replicators from the human β-globin locus initiate replication early during S-phase without LCR (Aladjem et al., *Science* 281:1005, 1998) and LCR can delay replication when inserted in a late-replicating site (Feng et al., *Mol Cell Biol* 25:3864, 2005). Current observations suggest that insertion of replicators can prevent this replication delay, further emphasizing that the replication effects of LCR are not limited to specific replicators and depend on chromosomal context.

Transcriptional control elements affect replication in other genomic regions. Late replication is generally associated with heterochromatin whereas early replication correlates with more accessible chromatin and active transcription (Lorincz et al., *Mol Cell Biol* 22:7572, 2002; Gilbert, *Curr Opin Cell Biol* 14:377, 2002). Specific examples of transcriptional control elements determining the replication profile include the Chinese hamster DHFR promoter affecting the location of initiation events within the DHFR locus (Kalejta et al., *Molecular Cell* 2:797, 1998; Saha et al., Genes Dev 18:397, 2004), promoters affecting initiation activity from ectopic c-myc insertions (30), tethering chromatin modifiers specifying the location of initiation events from the *Drosophila* chorion gene replicators (Aggarwal et al., *Nature* 430:372, 2004), and transcription activation at mid-blastula affects specification of replication origins in *Xenopus* egg extracts (Danis et al., *Nat Cell Biol* 6:721, 2004). However, while the activation of transcription in the above cases correlated with altered initiation patterns, the causal relationships between the location of initiation events and activation of transcription remain unclear. In the experiments described here, replication delay occurred before gene silencing, suggesting that the effects of LCR on replication timing were not directly mediated by changes in transcriptional activity. Observations in the murine immunoglobulin IgH locus, in which an advanced replication time of one of the two IgH alleles in pre-replicating B cells occurs prior to transcription (Zhou et al., *Proc Natl Acad Sci USA* 99: 13693, 2002), provide an example for changes in replication timing that precede changes in gene expression. Because the ability to prevent silencing was only observed in functional replicators, these studies provide direct evidence that functional mammalian replicators can affect chromatin condensation and modulate replication timing, probably via chromatin modifications.

An important implication of this study is that inclusion of replicators within transgenes integrated into the genome of the cell can stabilize gene expression and prevent gene silencing. Silencing vectors for gene therapy feature condensed chromatin, including methylated CpG sequences, deacetylated histone H3, and bound linker histone H1 (Ellis and Pannell, *Clin Genet* 59:17, 2001; Lorincz et al., *Mol Cell Biol* 22:7572, 2002; Yao et al., *Mol Ther* 10:27, 2004; Feng et al., *Mol Cell Biol* 21:298, 2001). The use of stronger promoters, such as EF1a, does not overcome silencing (Chong, et al., *Mol Cell Biol* 22:4667, 2002; Ramezani et al., *Front Biosci* 7:a29, 2002). Matrix-attachment region elements or insulator elements that overcome position effects may contribute to increase expression level of the gene therapeutic vector (Pawliuk et al., *Science* 294:2368, 2001; May et al., *Nature* 406:82, 2000; Lutzko et al., *J Virol* 77:7341, 2003). The prevention of gene silencing and replication delay by replicators may be important for the development of gene therapy vectors.

Example 2

In Vitro Prevention of Gene Silencing

This example describes a non-limiting method for preventing gene silencing and maintaining early replication of chromatin in vitro. Though the example is given in the context of expressing particular genes in the listed cells, it will be understood by one of ordinary skill in the art that the method could also be practiced in other cell types and for the expression of other transgenes.

Plasmids

Plasmid construction and transfections are performed using standard molecular biology techniques (Ausubel et al. *Current Protocols in Molecular Biology* (2006), John Wiley & Sons, Inc.). Rep-P (positions 59882 to 62187 of GenBank Accession Number U01317.1; SEQ ID NO: 2), Rep-I (positions 62187 to 64557 of GenBank Accession Number U01317.1), LMNB2 (positions 3691 to 4978 of GenBank Accession No. M94363), and mutated Rep-P (SEQ ID NO: 32) from the human β-globin locus were described previously (Wang et al., *Mol Cell Biol* 24:3373, 2004). Replicator sequences (such as full length Rep-P and mutated Rep-P) are inserted into, for instance, the HS432-β-promoter-β-globin plasmid using standard methodology; an example of such methodology is described above in Example 1.

Cell Culture and Transfections

Murine (murine erythroleukemia, MEL), human (erythroleukemia, HEL; leukemia, CEM; glioblastoma, M059K), and CV1 monkey kidney derived cell lines are maintained in growth medium, e.g., Dulbecco modified Eagle's medium (Invitrogen) supplemented with 10% heat-inactivated fetal calf serum. Targeted insertion of plasmid vectors into any of the above mammalian (target) cells is performed using RMCE (Feng et al., *J. Mol. Biol.* 292 (4): 779-785, 1999). With this technique, a cassette encoding for antibiotic-resistance markers flanked by inverted LoxP sites is first inserted in a single genomic site. The insertion might be random or targeted by homologous recombination. In the second step, a replacement cassette is transfected into cells in the presence of excess CRE, which catalyzes the replacement of the original cassette by the replacement cassette. The second replacement cassette includes replicators (Rep-P, Rep-I, MutRep-P, or LMNB2) adjacent to promoters and either the LCR from the human β-globin locus or two separate hypersensitive sites (HS2 and HS4) fused to a transgene of interest (for example, α-globin, β-globin, Von Willebrand Factor (VWF), or ADAMTS13 (a disintegrin and metalloproteinase with thrombospondin repeats).

The target cells are co-transfected by lipofectamine 2000 (Invitrogen) with 4 µg of an exchange plasmid containing the cassette of interest (such as Rep-P-human β-globin promoter-human α-globin-neo$^r$, Rep-P-human β-globin promoter-VWF-neo$^r$, Rep-P-human β-globin promoter-human β-globin-neo$^r$, Rep-P-human β-globin promoter-AD-AMTS13-neo$^r$, or the equivalent construct with the MutRep-P replicator). Equivalent constructs are made with the LMNB2 replicator sequence. These constructs were integrated either into the RL4, RL5, or RL6 insertion sites. RL6 is also in MEL cells, on chromosome 7 in the heterochromatin. Cells receiving the cassette present in the exchange plasmid are selected with neomycin, and replacement of the target cell DNA by the exchange cassette (integrated transgene construct) is then verified by PCR. Cells containing the plasmids at either of the three insertion sites are analyzed for gene expression. The effect of replicators on silencing will be assessed every two weeks, for example at 2, 4, 6, 8, 10, 12, 14, 16, 18, weeks or longer, or at 1, 2, 4, 6, 8, 10, 12, 16, 18, 24, 36 months or longer, post-transfection.

Replication Initiation Analyses

Replication initiation analyses are performed by isolating short, newly replicated DNA strands from asynchronously growing cells (Aladjem et al., *Science* 281:1005-9, 1998). Newly replicated DNA strands are identified by an RNA stretch at the 5' end, which makes the molecules resistant to digestion by lambda exonuclease. The abundance of sequences from the inserted transgenes in newly replicated DNA is quantified using real time PCR (Wang et al., *Mol. Cell. Biol.*, 24:3373-86, 2004).

Replication Timing Analyses and Human β-Globin Expression

Replication timing analyses and levels of transgene expression are measured periodically, for instance, at 2, 7, 14, 21, 28 days or longer, or at 1, 2, 4, 6, 8, 10, 12, 16, 18 months or longer, post-transfection.

Replication timing analyses are performed, for instance, as described in Example 1. Cell cycle fractions are sorted using a Vantage fluorescence-activated cell sorter or elutriator. Newly replicated, BrdU-substituted DNA is isolated by immunoprecipitation with anti-BrdU antibodies as described (Lin et al., *Curr Biol* 13:1019, 2003). Each sample is subject to two sequential rounds of immunoprecipitation, washes, and DNA purification. BrdU-incorporated *Drosophila* genomic DNA is added as an internal control to each sample before immunoprecipitation. The quantity of newly replicated (BrdU-substituted) DNA is determined with OligoGreen and the abundance of mitochondrial DNA sequences (mMT primers) is used to verify that each fraction contained similar quantities of amplifiable DNA strands. Samples containing 8 ng DNA are amplified with a series of human β-globin primer-probe combinations and analyzed by real-time PCR on an ABI 7900. The quantity of an amplified sequence is calculated using genomic DNA standards with a standard curve from 0.005 to 50 ng per reaction. Each measurement is performed in triplicate.

Transgene expression in the mammalian cells transfected with the cassettes is measured by standard techniques, such as immunocytochemical, in-situ hybridization, and Northern blot methods. Cells having the Rep-I, LMNB2, or full-length Rep-P cassette maintain transgene expression and early S phase replication of the DNA encoding the transgene longer than cells having the MutRep-P cassette. Silencing in all three insertion sites is accompanied by a replication delay, whereas early replication persisted in cells in which silencing is prevented by the inclusion of replicators in the transgene construct.

Chromatin Immunoprecipitations

Chromatin immunoprecipitations are performed by exposing cells to formaldehyde to cross-link DNA and proteins. The crosslinked chromatin is isolated, randomly fragmented by sonication, and reacted with antibodies against specific proteins that might bind chromosomal DNA sequences. The abundance of sequences from the inserted transgenes in chromatin precipitated from cross-linked chromatin by specific antibodies is quantified using real time PCR.

Expression of Transgenes

Gene silencing is monitored by FACS analysis using antibodies against the transgene of interest. Cells with transgenes that do not include replicators undergo transcriptional silencing after three to four months in culture, whereas the cells with plasmids including the replicator do not.

Example 3

This example describes a non-limiting method for preventing or delaying gene silencing and maintaining early replication of chromatin in vitro. Though the example is given in the context of expressing β-globin in CD34$^+$ cells, it will be understood by one of ordinary skill in the art that the method could also be practiced in other cells and for the expression of other transgenes.

Plasmids

Rep-P (positions 59882-62187 of GenBank Accession Number U01317.1; SEQ ID NO: 2) and mutated Rep-P (SEQ ID NO: 32) from the human β-globin locus were described previously (Wang et al., *Mol Cell Biol* 24:3373, 2004). Replicator sequences (such as full length Rep-P and mutated Rep-P) are inserted into, for instance, the HS432-β-promoter-β-globin plasmid using standard methodology; an example of such methodology is described above in Example 1.

Cell Culture and Transfections

Murine CD34$^+$ cells are maintained in growth medium, e.g., Dulbecco modified Eagle's medium (invitrogen) supplemented with 10% heat-inactivated fetal calf serum. The transgene construct is integrated into the genome of the cell, for instance using Cre recombinase-mediated cassette exchange as described in Example 1. The target cells (murine CD34$^+$ cells in this example) are co-transfected by lipofectamine 2000 (Invitrogen) with 4 µg of an exchange plasmid containing the cassette of interest (such as Rep-P-human β-globin promoter-human β-globin-neo$^r$ or MutRep-P-human β-globin promoter-human β-globin-neo$^r$). Cells receiving the cassette present in the exchange plasmid are selected with neomycin, and replacement of the CD34⁺ DNA by the exchange cassette is then verified by PCR.

Replication Timing Analyses and Human β-Globin Expression

Replication timing analyses and levels of human β-globin expression are measured periodically, for instance, at 2, 7; 14, 21, and 28 days and at 1, 2, 4, 6, 8, 10, 12, 16, and 18 months post-transfection.

Replication timing analyses are performed, for instance, as described in Example 1. Cell cycle fractions are sorted using a Vantage fluorescence-activated cell sorter or elutriator. Newly replicated, BrdU-substituted DNA is isolated by immunoprecipitation with anti-BrdU antibodies as described (Lin et al., *Curr Biol* 13:1019, 2003). Each sample is subject to two sequential rounds of immunoprecipitation, washes, and DNA purification. BrdU-incorporated *Drosophila* genomic DNA is added as an internal control to each sample before immunoprecipitation. The quantity of newly replicated (BrdU-substituted) DNA is determined with OligoGreen and the abundance of mitochondrial DNA sequences (mMT primers) is used to verify that each fraction contained similar quantities of amplifiable DNA strands. Samples containing 8 ng DNA are amplified with a series of human β-globin primer-probe combinations and analyzed by real-time PCR on an ABI 7900. The quantity of an amplified sequence is calculated using genomic DNA standards with a standard curve from 0.005 to 50 ng per reaction. Each measurement is performed in triplicate.

Human β-globin expression in murine CD34⁺ cells transfected with the MutRep-P cassette or the full-length Rep-P cassette is measured by standard techniques, such as immunocytochemical, in-situ hybridization, and Northern blot methods.

Cells having the full-length Rep-P cassette will maintain human β-globin expression and early S phase replication of the DNA encoding β-globin longer than cells having the MutRep-P cassette.

Example 4

Transduction of Human CD34⁺ Cells Using Adenoviral Vectors

Ex vivo methods can be used to introduce a transgene construct of interest into autologous or heterologous cells, which can be subsequently introduced into a subject to treat a disease. For example, ex vivo methods for introducing an adenoviral vector containing the Rep-P-human β-globin promoter-human β-globin-neo$^r$ cassette (Rep-P cassette) in a subject having sickle cell anemia involve transducing CD34⁺ cells ex vivo, and then introducing the transduced CD34⁺ cells into the subject. Rep-P prevents silencing of the β-globin gene in the transduced CD34⁺ cells, thereby maintaining expression of the gene. Rep-P (positions 59882-62187 of GenBank Accession Number U01317.1; SEQ ID NO: 2) from the human β-globin locus is described previously (Wang et al., *Mol Cell Biol* 24:3373, 2004). Adenovirus particles having adenoviral vectors including the Rep-P cassette are used to transduce autologous cells isolated from a subject having sickle cell anemia. Alternatively, the cells are heterologous cells, such as CD34⁺ cells stored in an umbilical cord blood bank or a bone marrow bank. Transduced CD34⁺ cells are delivered to the subject by standard methods.

This example describes a non-limiting method of preventing gene silencing in a subject, using cells that have had a transgene construct introduced ex vivo with an adenoviral vector.

CD34⁺ Cell Purification:

By way of example, 15-20 mL bone marrow aspirates are obtained from a subject having sickle cell anemia after informed consent. Cells are diluted 1:3 in phosphate buffered saline (PBS, Gibco-BRL), 30 mL are layered over 15 mL Histopaque-1077 (Sigma) and centrifuged for 30 minutes at 300 RCF. The mononuclear interface layer is collected and washed in PBS. CD34⁺ cells are enriched from the mononuclear cell preparation using an affinity column per manufacturers' instructions (CellPro, Inc, Bothel, Wash.). After enrichment, the purity of CD34⁺ cells is expected to be 70% on average, as determined by flow cytometric analysis using anti CD34 monoclonal antibody conjugated to fluorescein (Becton Dickinson, San Jose, Calif.).

Cells are resuspended at 40,000 cells/mL in X-Vivo 10 media (Bio-Whittaker, Walkersville, Md.) and 1 mL is plated in 12-well tissue culture plates (Costar). The growth factor IL-3 is added at 100 ng/mL to the cells. Cells are incubated at 37° C. for 8-14 days at 5% $CO_2$ in a 37° C. humidified incubator. At the end of the culture period a total cell count is obtained.

Transduction and Administration of CD34⁺ Cells

CD34⁺ cells are plated at a concentration of 5×10⁴ cells per well of 24-well plates, and maintained in culture for 24 hours. CD34⁺ cells are subsequently exposed to 1000 adenovirus particles having adenoviral vectors including the Rep-P cassette. Forty-eight hours after virus addition, cells are harvested and tested for integration of the Rep-P cassette into the CD34⁺ cell genome using standard PCR techniques and for human β-globin expression using standard immunocytochemistry and Northern blot techniques. Transduced CD34⁺ cells expressing β-globin are administered intravenously into the subject having sickle cell anemia using standard protocols.

This disclosure provides a method of inhibiting gene silencing. It will be apparent that the precise details of the methods described may be varied or modified without departing from the spirit of the described invention. We claim all such modifications and variations that fall within the scope and spirit of the claims below.

Example 5

Transduction of Human CD34⁺ Cells Using Adeno-Associated Virus ("AAV") Vectors

This example describes a non-limiting method of preventing or delaying gene silencing in a subject, using cells that have had a transgene construct introduced ex vivo with an adeno-associated virus (AAV) vector.

Recombinant viral vectors containing the transgene construct (including a replicator sequence and a transgene sequence of interest) are encapsidated using a helper virus. Briefly, semi-confluent cultured 293T cells are infected with helper virus and transfected 1 hour post-infection with 20 μg of the vector plasmids by calcium phosphate co-precipitation (CellPhect; Pharmacia Biotech, Uppsala, Sweden). AAV-encoded rep (DNA replication) and cap (capsid proteins) gene functions are provided in trans. Cells are harvested 72 hours post-transfection and are lysed by three cycles of freeze-thawing and sonication. Vector stocks are treated to digest residual plasmid and cellular DNA and particle titers are determined by dot blot analysis. Functional titers are determined by quantitation of specific alkaline phosphatase expressing cells and neomycin resistant (NeoR) colonies after serial dilutions on cultured cells. All helper virus stocks and cell lines are screened for wild-type AAV contamination.

CD34+ cells are purified and isolated from a subject, as described in Example 4, and transduced immediately upon isolation. Transductions are performed by the direct addition of vector to cells and left undisturbed for 24 to 48 hours, after which cells are washed and replated. Cells are then harvested and tested for integration of the Rep-P cassette into the CD34+ cell genome using standard PCR techniques and for transgene expression using standard immunocytochemistry and Northern blot techniques. Transduced CD34+ cells expressing the transgene are administered into the subject using standard protocols.

Example 6

Transduction of Mammalian Stem Cells Using Lentiviral Vectors

This example describes a non-limiting method of preventing gene silencing in a subject, using stem cells that have had a transgene construct introduced ex vivo with a lentiviral vector.

Lentiviral vector stocks are produced by transient transfection into 293T cells. Briefly, a total of $5 \times 10^6$ 293T cells are seeded in 10-cm-diameter dishes 24 hours prior to transfection in Iscove modified Dulbecco culture medium (JRH Biosciences) with 10% fetal bovine serum, penicillin (100 IU/ml), and streptomycin (100 µg/ml) in a 5% $CO_2$ incubator, and the culture medium is changed 2 hours prior to transfection. A total of 20 µg of plasmid DNA is used for the transfection of one dish: 3.5 µg of the envelope plasmid pMD.G, 6.5 µg of packaging plasmid, and 10 µg of transfer vector plasmid (including a replicator sequence and a transgene sequence of interest). A precipitate is formed and is immediately added to the cultures. The medium is replaced after 14 to 16 hours; the conditioned medium is collected after another 24 hours, cleared by low-speed centrifugation, and filtered through 0.22-µm-pore-size cellulose acetate filters. Vector batches are tested for the absence of replication-competent virus by monitoring p24 antigen expression in the culture medium of transduced SupT1 lymphocytes for 3 weeks.

Filtered vector-containing medium is added to the seeded mammalian stem cells, for example hematopoietic CD34+ cells or embryonic stem cells, and is left until cells are analyzed 48 to 60 hours later. Cells are then harvested and tested for integration of the Rep-P cassette into the stem cell genome using standard PCR techniques and for transgene expression using standard immunocytochemistry and Northern blot techniques. Transduced stem cells expressing the transgene are administered into the subject using standard protocols.

This disclosure provides a method of inhibiting gene silencing. It will be apparent that the precise details of the methods described may be varied or modified without departing from the spirit of the described invention. We claim all such modifications and variations that fall within the scope and spirit of the claims below.

---

We claim:

1. An ex vivo method of inhibiting silencing of a gene in a cell, comprising:
   (A) introducing into the cell a transgene construct comprising:
      (i) a coding nucleic acid sequence to be expressed in the cell; and
      (ii) a metazoan replicator nucleic acid sequence, wherein the metazoan replicator nucleic acid sequence integrates into a host genome with the coding nucleic acid sequence and:
         (a) is between 1.2 kb and 5.8 kb in length;
         (b) comprises a nucleic acid sequence at least 95% identical to the nucleic acid sequence set forth as SEQ ID NO: 1, SEQ ID NO: 2, SEQ ID NO: 3, SEQ ID NO: 4, SEQ ID NO: 5, SEQ ID NO: 6, or SEQ ID NO: 7;
         (c) confers initiation of DNA replication in cis at ectopic chromosomal sites;
         (d) maintains DNA replication of the transgene construct in early S phase;
         (e) inhibits chromatin condensation; and
         (f) inhibits silencing of expression of the coding nucleic acid sequence; and
   (B) detecting expression of the coding nucleic acid sequence at least six weeks after introducing the metazoan replicator nucleic acid sequence into the cell, compared to a control cell that does not comprise the replicator nucleic acid sequence, thereby inhibiting silencing of the gene in the cell.

2. The method of claim 1, wherein the cell is a mammalian cell.

3. The method of claim 2, wherein the mammalian cell is human.

4. The method of claim 1, wherein the transgene construct is introduced into the host cell genome by homologous recombination or recombinase-mediated cassette exchange.

5. An improved ex vivo method of expressing a coding nucleic acid sequence in a cell, wherein a transgene construct comprising the coding nucleic acid sequence is integrated into a host cell genome, wherein the improvement comprises:
   (A) introducing into the cell a metazoan replicator nucleic acid sequence comprising AT-rich sequences, wherein the metazoan replicator nucleic acid sequence integrates into the host cell genome at the same site as the transgene construct and:
      (i) is between 1.2 kb and 5.8 kb in length;
      (ii) comprises a nucleic acid sequence at least 95% identical to the nucleic acid sequence set forth as SEQ ID NO: 1, SEQ ID NO: 2, SEQ ID NO: 3, SEQ ID NO: 4, SEQ ID NO: 5, SEQ ID NO: 6, or SEQ ID NO: 7;
      (iii) confers initiation of DNA replication in cis at ectopic chromosomal sites;
      (iv) alters timing of DNA replication of the transgene construct from late S phase to early S phase;
      (v) inhibits chromatin condensation; and
      (vi) inhibits silencing of the coding nucleic acid sequence; and
   (B) detecting expression of the coding nucleic acid sequence at least six weeks after introducing the metazoan replicator nucleic acid sequence into the cell, compared to a control cell that does not comprise the replicator nucleic acid sequence, thereby improving the method of expressing a coding nucleic acid sequence in the cell.

6. The method of claim 5, wherein the coding nucleic acid sequence encodes a therapeutic product.

7. The method of claim 5, wherein the cell is a mammalian cell.

8. The method of claim 7, wherein the mammalian cell is human.

9. The method of claim 5, wherein the transgene construct comprises an adenoviral or a retroviral sequence.

10. The method of claim 5, wherein the transgene construct is introduced into the host cell genome by homologous recombination or recombinase-mediated cassette exchange.

11. The method of claim 1, wherein the transgene construct comprises an adenoviral or a retroviral sequence.

12. The method of claim 1, wherein the cell is an isolated cell.

13. The method of claim 1, wherein the metazoan replicator comprises the nucleic acid sequence set forth as SEQ ID NO: 1, SEQ ID NO: 2, SEQ ID NO: 3, SEQ ID NO: 4, SEQ ID NO: 5, SEQ ID NO: 6, or SEQ ID NO: 7.

14. The method of claim 13, wherein the metazoan replicator comprises the nucleic acid sequence set forth as SEQ ID NO: 1, SEQ ID NO: 3, or SEQ ID NO: 4.

15. The method of claim 5, wherein the cell is an isolated cell.

16. The method of claim 5, wherein the metazoan replicator comprises the nucleic acid sequence set forth as SEQ ID NO: 1, SEQ ID NO: 2, SEQ ID NO: 3, SEQ ID NO: 4, SEQ ID NO: 5, SEQ ID NO: 6, or SEQ ID NO: 7.

17. The method of claim 16, wherein the metazoan replicator comprises the nucleic acid sequence set forth as SEQ ID NO: 1, SEQ ID NO: 3, or SEQ ID NO: 4.

18. A method of inhibiting silencing of a gene in an isolated cell in vitro, comprising:
   (A) introducing into the cell a transgene construct comprising:
      (i) a coding nucleic acid sequence to be expressed in the cell; and
      (ii) a metazoan replicator nucleic acid sequence, wherein the metazoan replicator nucleic acid sequence is between 1.2 kb and 5.8 kb in length; comprises the nucleic acid sequence set forth as SEQ ID NO: 1, SEQ ID NO: 3, or SEQ ID NO: 4; maintains DNA replication of the transgene construct in early S phase, inhibits chromatin condensation, and inhibits silencing of expression of the coding nucleic acid sequence; and
   (B) detecting expression of the coding nucleic acid sequence at least six weeks after introducing the metazoan replicator nucleic acid sequence into the cell, compared to a control cell that does not comprise the replicator nucleic acid sequence, thereby inhibiting silencing of the gene in the cell.

* * * * *